US012029820B2

(12) United States Patent
Cobb, Jr. et al.

(10) Patent No.: US 12,029,820 B2
(45) Date of Patent: Jul. 9, 2024

(54) SUSTAINED RELEASE COMPOSITIONS OF 4-AMINOPYRIDINE

(71) Applicant: Acorda Therapeutics, Inc., Pearl River, NY (US)

(72) Inventors: Joseph E. Cobb, Jr., Greenville, NC (US); Thomas B. Gold, Greenville, NC (US); Rohini D'Souza, Pomona, NY (US); Susan L. Way, Danbury, CT (US)

(73) Assignee: Acorda Therapeutics, Inc., Pearl River, NY (US)

( * ) Notice: Subject to any disclaimer, the term of this patent is extended or adjusted under 35 U.S.C. 154(b) by 26 days.

(21) Appl. No.: 17/374,285

(22) Filed: Jul. 13, 2021

(65) Prior Publication Data
US 2021/0338590 A1 Nov. 4, 2021

Related U.S. Application Data

(63) Continuation of application No. 17/111,845, filed on Dec. 4, 2020, now abandoned, which is a continuation of application No. 16/827,130, filed on Mar. 23, 2020, now abandoned, which is a continuation of application No. 15/764,160, filed as application No. PCT/US2016/054109 on Sep. 28, 2016, now abandoned.

(60) Provisional application No. 62/234,455, filed on Sep. 29, 2015.

(51) Int. Cl.
*A61K 9/28* (2006.01)
*A61K 9/20* (2006.01)
*A61K 31/4409* (2006.01)

(52) U.S. Cl.
CPC .......... *A61K 9/2866* (2013.01); *A61K 9/2009* (2013.01); *A61K 9/2013* (2013.01); *A61K 9/2027* (2013.01); *A61K 9/2031* (2013.01); *A61K 9/2095* (2013.01); *A61K 9/2893* (2013.01); *A61K 31/4409* (2013.01)

(58) Field of Classification Search
CPC .............. A61K 9/2866; A61K 9/2893; A61K 31/4409; A61K 9/2009; A61K 9/2013; A61K 9/2027; A61K 9/2031; A61K 9/2095
See application file for complete search history.

(56) References Cited

U.S. PATENT DOCUMENTS

| 5,068,112 | A | 11/1991 | Samejima et al. |
| 5,254,347 | A | 10/1993 | Samejima et al. |
| 5,370,879 | A | 12/1994 | Masterson et al. |
| 5,540,938 | A | 7/1996 | Masterson et al. |
| 5,837,379 | A | 11/1998 | Chen et al. |
| 6,183,777 | B1 | 2/2001 | Chen et al. |
| 6,500,457 | B1 | 12/2002 | Midha et al. |
| 6,703,044 | B1 | 3/2004 | Pinhasi et al. |
| 6,960,357 | B2 | 11/2005 | Chopra |
| 7,611,722 | B2 | 11/2009 | Lerner et al. |
| 7,632,520 | B2 | 12/2009 | Khandelwal |
| 8,007,826 | B2 | 8/2011 | Blight et al. |
| 8,153,159 | B2 | 4/2012 | Parikh et al. |
| 8,354,437 | B2 | 1/2013 | Blight et al. |
| 8,383,151 | B2 | 2/2013 | Jahagirdar et al. |
| 8,633,134 | B2 | 1/2014 | Kaiser et al. |
| 8,652,527 | B1 | 2/2014 | Betterman et al. |
| 8,663,655 | B2 | 3/2014 | Boyaval et al. |
| 8,858,993 | B2 | 10/2014 | Gold et al. |
| 8,889,190 | B2 | 11/2014 | Betterman et al. |
| 8,927,025 | B2 | 1/2015 | Hamed |
| 9,005,636 | B2 | 4/2015 | Suh et al. |
| 9,101,545 | B2 | 8/2015 | Betterman et al. |
| 2001/0038852 | A1 | 11/2001 | Kolter et al. |
| 2003/0133982 | A1 | 7/2003 | Heimlich et al. |
| 2005/0106242 | A1 | 5/2005 | Yan et al. |
| 2005/0106251 | A1 | 5/2005 | Langridge et al. |
| 2005/0112198 | A1 | 5/2005 | Challapalli et al. |
| 2005/0112202 | A1 | 5/2005 | Lerner et al. |
| 2005/0250838 | A1 | 11/2005 | Challapalli et al. |
| 2005/0276851 | A1 | 12/2005 | Cunningham et al. |
| 2006/0057204 | A1 | 3/2006 | Penhasi et al. |
| 2006/0110454 | A1 | 5/2006 | Kshirsager et al. |
| 2006/0280795 | A1 | 12/2006 | Penhasi et al. |
| 2007/0122480 | A1 | 5/2007 | Cho et al. |
| 2007/0184115 | A1 | 8/2007 | Mamajiwalla et al. |
| 2007/0237818 | A1 | 10/2007 | Malcolm et al. |
| 2007/0269511 | A1 | 11/2007 | Bockbrader et al. |
| 2008/0020041 | A1 | 1/2008 | Ayres |
| 2008/0187579 | A1 | 8/2008 | Bhat et al. |
| 2010/0008987 | A1 | 1/2010 | Chowdary et al. |
| 2010/0055173 | A1 | 3/2010 | Penhasi et al. |
| 2010/0151015 | A1 | 6/2010 | Venkatesh et al. |

(Continued)

FOREIGN PATENT DOCUMENTS

RU 2536269 C1 12/2014
WO WO 2004/037226 A2 5/2004
(Continued)

OTHER PUBLICATIONS

U.S. Appl. No. 17/531,032, filed Nov. 19, 2021, Cobb et al.
Ampyra® (dalfampridine), Acorda Therapeutics, Inc., Prescribing Information, Jan. 2010. http://ampyra.com/local/files/PI.pdf (last accessed Nov. 3, 2010) (6 pages).
(Continued)

*Primary Examiner* — Shirley V Gembeh
(74) *Attorney, Agent, or Firm* — Jones Day

(57) ABSTRACT

The present invention generally relates to sustained release 4-aminopyridine tablets, which include a core and a coating. The sustained release tablets of the invention are generally suitable for once daily oral administration for the treatment of neurological disorders.

32 Claims, 6 Drawing Sheets

(56) References Cited

U.S. PATENT DOCUMENTS

| | | |
|---|---|---|
| 2010/0247646 A1 | 9/2010 | Prasad et al. |
| 2010/0330172 A1 | 12/2010 | Mooney et al. |
| 2011/0123613 A1 | 5/2011 | Bhat et al. |
| 2011/0159094 A1 | 6/2011 | Onn et al. |
| 2011/0287094 A1 | 11/2011 | Penhasi et al. |
| 2013/0040942 A1 | 2/2013 | Cowen et al. |
| 2013/0045276 A1 | 2/2013 | Cunningham et al. |
| 2013/0078290 A1 | 3/2013 | Pilgaonakar et al. |
| 2013/0171256 A1 | 7/2013 | Hamed |
| 2013/0202705 A1 | 8/2013 | Hamed |
| 2014/0179749 A1 | 6/2014 | Lorenz et al. |
| 2014/0200200 A1 | 7/2014 | Piazza et al. |
| 2014/0271839 A1 | 9/2014 | Betterman et al. |
| 2014/0287037 A1 | 9/2014 | Betterman et al. |
| 2014/0364425 A1 | 12/2014 | Cowen et al. |
| 2015/0030676 A1 | 1/2015 | Venkatesh et al. |
| 2015/0104507 A1 | 4/2015 | Cawello et al. |
| 2015/0231084 A1 | 8/2015 | Kumar et al. |
| 2015/0265544 A1 | 9/2015 | Betterman et al. |
| 2015/0328168 A1 | 11/2015 | Daviaud-Venet et al. |
| 2016/0002259 A1 | 1/2016 | Pasternak et al. |
| 2016/0038426 A1 | 2/2016 | Betterman et al. |
| 2016/0051476 A1 | 2/2016 | Pilgaonkar et al. |
| 2017/0071923 A1 | 3/2017 | Yang et al. |
| 2018/0344649 A1 | 12/2018 | Cobb et al. |
| 2020/0108016 A1 | 4/2020 | Cobb et al. |
| 2020/0253880 A1 | 8/2020 | Cobb et al. |
| 2021/0085614 A1 | 3/2021 | Cobb et al. |
| 2022/0323362 A1 | 10/2022 | Cobb et al. |

FOREIGN PATENT DOCUMENTS

| | | |
|---|---|---|
| WO | WO 2004/082684 A1 | 9/2004 |
| WO | WO 2005/030179 A1 | 4/2005 |
| WO | WO 2005/107716 A1 | 11/2005 |
| WO | WO 2006/044202 A2 | 4/2006 |
| WO | WO 2006/046256 A1 | 5/2006 |
| WO | WO 2006/121521 A2 | 11/2006 |
| WO | WO 2007/014061 A2 | 2/2007 |
| WO | WO 2007/078895 A2 | 7/2007 |
| WO | WO 2007/138557 A2 | 12/2007 |
| WO | WO 2007/150074 A2 | 12/2007 |
| WO | WO 2008/023390 A2 | 2/2008 |
| WO | WO 2008/044236 A2 | 4/2008 |
| WO | WO 2008/094440 A1 | 8/2008 |
| WO | WO 2009/118763 A1 | 10/2009 |
| WO | WO 2010/008925 A1 | 1/2010 |
| WO | WO 2010/077927 A1 | 7/2010 |
| WO | WO 2011/151708 A1 | 12/2011 |
| WO | WO 2012/010347 A1 | 1/2012 |
| WO | WO 2012/014052 A2 | 2/2012 |
| WO | WO 2012/139876 A1 | 10/2012 |
| WO | WO 2012/160006 A1 | 11/2012 |
| WO | WO 2013/009142 A2 | 1/2013 |
| WO | WO 2014/060952 A1 | 4/2014 |
| WO | WO 2014/091437 A1 | 6/2014 |
| WO | WO 2014/093475 A1 | 6/2014 |
| WO | WO 2014/143380 A1 | 9/2014 |
| WO | WO 2014/151797 A | 9/2014 |
| WO | WO 2015/063670 A1 | 5/2015 |
| WO | WO 2015/189279 A1 | 12/2015 |
| WO | WO 2017/058869 A1 | 4/2017 |
| WO | WO 2018/186866 A1 | 10/2018 |

OTHER PUBLICATIONS

Anand et al., 2011, "Dissolution testing for generic drugs: an FDA perspective", AAPS J, 13(3):328-335.
FDA Guidance for Industry: Bioavailability and Bioequivalence Studies for Orally Administered Drug Products—General Considerations (Mar. 2003) (pp. 1-23).
FDA Guidance for Industry: Food-Effect Bioavailability and Fed Bioequivalence Studies (Dec. 2002) (pp. 1-9).
FDA Guidance for Industry: Pharmacokinetics in patients with impaired renal function—study design, data analysis, and impact on dosing and labeling (Mar. 2010) (pp. 1-18).
International Preliminary Report on Patentability dated Apr. 3, 2018 of International application No. PCT/US2016/054109 (10 pages).
International Search Report dated Dec. 16, 2016 of International application No. PCT/US2016/054109 (4 pages).
International Search Report dated Jan. 24, 2018 of International application No. PCT/US2017/026360 (5 pages).
Pati et al., 2016, "Comparative study of effect of various types of polymers on extended release of tapentadol HCL", International Journal Of Pharmacy & Technology, 8(2):12762-12775.
Written Opinion dated Dec. 16, 2016 of International application No. PCT/US2016/054109 (8 pages).
Written Opinion dated Jan. 24, 2018 of International application No. PCT/US2017/026360 (7 pages).
Office Action dated Sep. 25, 2019 in U.S. Appl. No. 15/764,160 (8 pages).
Office Action dated May 28, 2021 in U.S. Appl. No. 16/500,944 (14 pages).
U.S. Appl. No. 18/488,349, filed Oct. 17, 2023, Cobb et al.
Office Action dated Apr. 21, 2023 in U.S. Appl. No. 17/531,032 (15 pages).

SUSTAINED RELEASE COMPOSITIONS OF 4-AMINOPYRIDINE

CROSS-REFERENCE TO RELATED APPLICATIONS

This application is a continuation of U.S. patent application Ser. No. 17/111,845, filed Dec. 4, 2020, which is a continuation of U.S. patent application Ser. No. 16/827,130, filed Mar. 23, 2020, which is a continuation of U.S. patent application Ser. No. 15/764,160, which is a national stage of International Patent Application No. PCT/US2016/054109, filed Sep. 28, 2016, which claims the benefit of U.S. Provisional Patent Application No. 62/234,455, filed Sep. 29, 2015, U.S. patent application Ser. No. 17/111,845 is incorporated by reference herein in its entirety.

1 FIELD OF THE INVENTION

The present invention generally relates to sustained release 4-aminopyridine tablets, which include a core and a coating. The sustained release tablets of the invention are generally suitable for once daily oral administration for the treatment of neurological disorders.

2 BACKGROUND OF THE INVENTION

4-Aminopyridine is a potassium (K+) channel blocker approved by the U.S. Food and Drug Administration as a treatment for patients with multiple sclerosis to improve walking. Dalfampridine is the United States Adopted Name (USAN) for the chemical 4-aminopyridine, which has a molecular formula of $C_5H_6N_2$ and molecular weight of 94.1; the former USAN name for this compound was fampridine (which remains the International Nonproprietary Name). The terms "dalfampridine", "fampridine" and "4-aminopyridine" will be used throughout this specification to refer to the active drug substance.

Studies of 4-aminopyridine (dalfampridine, fampridine) have been conducted using intravenous (i.v.) administration and immediate-release (IR) oral capsule formulations in addition to controlled-release or sustained-release formulations. Administration of IR capsules resulted in rapid and short-lasting peaks of 4-aminopyridine in the plasma. Early pharmacokinetic studies were conducted using an immediate release (IR) formulation for oral administration, which consisted of 4-aminopyridine powder in a gelatin-based capsule or oral solution. Administration resulted in rapidly changing 4-aminopyridine plasma levels that were not well tolerated. A sustained-release matrix tablet (known as Fampridine-SR or AMPYRA®, Acorda Therapeutics, Ardsley, NY) was then developed. The sustained release matrix tablet showed improved stability and an appropriate pharmacokinetic profile for twice-daily dosing. Sustained release compositions of 4-aminopyridine and related use of such compositions are set forth, e.g., in U.S. Pat. Nos. 5,370,879; 5,540,938; 8,007,826; 8,354,437; 8,663,655; International Publication WO 2012/10347, and International Publication WO 2014/093475. For example, suitable formulations, methods of manufacture, pharmacokinetic characteristics of sustained release aminopyridine compositions and methods of treating various neurological disorders are further described in U.S. Pat. No. 8,007,826 entitled "Sustained Release Aminopyridine Composition" issued on Aug. 30, 2011; and U.S. Pat. No. 8,354,437 entitled "Methods of Using Sustained Release Aminopyridine Compositions" issued on Jan. 15, 2013.

Provided herein are once daily sustained release 4-aminopyridine tablets that deliver a therapeutically effective amount of the active agent over 24 hours for the treatment of neurological disorders.

3 SUMMARY OF THE INVENTION

Provided herein is a sustained release tablet comprising:
(a) a compressed core, said compressed core comprising 4-aminopyridine, a polyethylene oxide with a molecular weight between about 1,000,000 and 10,000,000, and a mixture comprising polyvinyl acetate and polyvinyl pyrrolidone; and
(b) an amount of an ethylcellulose coat surrounding said compressed core, said amount of the ethylcellulose coat being in the range of about 5% w/w to about 10% w/w of the compressed core.

Provided herein is a sustained release tablet comprising:
(a) a compressed core, said compressed core comprising 4-aminopyridine, a polyethylene oxide with a molecular weight between about 1,000,000 and 10,000,000, and a mixture comprising polyvinyl acetate and polyvinyl pyrrolidone; and
(b) an amount of an ethylcellulose coat surrounding said compressed core, wherein the ratio of the amount of the ethylcellulose coat to the amount of 4-aminopyridine in the compressed core is in the range of about 0.5:1 to about 3:1; wherein for calculating said ratio, the amount of the ethylcellulose coat is the weight percentage of the ethylcellulose coat by weight of the compressed core, and the amount of 4-aminopyridine is the weight percentage of 4-aminopyridine by weight of the compressed core.

Provided herein is a sustained release tablet comprising:
(a) a compressed core, said compressed core comprising 4-aminopyridine, a polyethylene oxide with a molecular weight between about 1,000,000 and 10,000,000, and a mixture comprising polyvinyl acetate and polyvinyl pyrrolidone; and
(b) an amount of an ethylcellulose coat surrounding said compressed core, wherein the ratio of the amount of the ethylcellulose coat to the amount of 4-aminopyridine in the compressed core is in the range of about 0.1:1 to about 0.7:1; wherein for calculating said ratio, the amount of the ethylcellulose coat is the weight percentage of the ethylcellulose coat by weight of the compressed core, and the amount of 4-aminopyridine is the weight in milligrams of 4-aminopyridine.

In one embodiment, the sustained release tablet provided herein is the product of a process comprising a curing step after coating the compressed core with ethylcellulose, and wherein said curing step comprises heating the coated compressed core to a temperature above 23° C. for a period of time of at least 15 minutes.

In one embodiment of the sustained release tablet provided herein, the curing step comprises exposing the coated compressed core to a temperature in the range of 40-70° C. for a period of time of at least 1 hour.

In one embodiment of the sustained release tablet provided herein, the curing step comprises exposing the coated compressed core to a temperature in the range of 50-60° C. for a period of time of at least 1 hour.

Provided herein is a sustained release tablet comprising:
(a) a compressed core, said compressed core comprising 4-aminopyridine, a polyethylene oxide with a molecular weight between about 1,000,000 and 10,000,000, and a mixture comprising polyvinyl acetate and polyvinyl pyrrolidone; and (b) an amount of an ethylcellulose coat surrounding said compressed core, said amount of the ethylcellulose coat being in the range of about 8% w/w to about 10% w/w of the tablet, wherein said tablet is the product of a process comprising a curing step after coating the compressed core with ethylcellulose, and wherein said curing step comprises heating the coated compressed core to a temperature above 23° C. for a period of time of at least 15 minutes.

In one embodiment of the sustained release tablet provided herein, the mixture comprising polyvinyl acetate and polyvinyl pyrrolidone further comprises one or more pharmaceutically acceptable excipients.

In one embodiment of the sustained release tablet provided herein, the mixture comprising polyvinyl acetate and polyvinyl pyrrolidone comprises 70-90% polyvinyl acetate and 15-20% polyvinyl pyrrolidone.

In one embodiment of the sustained release tablet provided herein, the mixture comprising polyvinyl acetate and polyvinyl pyrrolidone further comprises a surfactant.

In one embodiment of the sustained release tablet provided herein, the mixture comprising polyvinyl acetate and polyvinyl pyrrolidone further comprises silica.

In one embodiment of the sustained release tablet provided herein, the mixture comprising polyvinyl acetate and polyvinyl pyrrolidone consists of about 80% polyvinyl acetate, about 19% polyvinyl pyrrolidone, about 0.8% sodium lauryl sulfate, and about 0.2% silica.

In one embodiment of the sustained release tablet provided herein, the compressed core comprising 4-aminopyridine further comprises a filler and a lubricant. In one embodiment, the filler is dibasic calcium phosphate dihydrate, and the lubricant is magnesium stearate.

In one aspect, provided herein is a sustained release tablet comprising:

(a) a compressed core, wherein said compressed core comprises: (i) 4-aminopyridine, (ii) a polyethylene oxide with a molecular weight between about 1,000,000 and 10,000,000, (iii) a mixture consisting of about 80% polyvinyl acetate, about 19% polyvinyl pyrrolidone, about 0.8% sodium lauryl sulfate, and about 0.2% of silica, (iv) dibasic calcium phosphate dihydrate, and (v) magnesium stearate; and (b) an amount of an ethylcellulose coat surrounding said compressed core, said amount of the ethylcellulose coat being in the range of about 5% w/w to about 10% w/w of the compressed core, wherein the amount of 4-aminopyridine is in the range of about 4% w/w to about 6% w/w of the compressed core.

In one embodiment of the sustained release tablet provided herein, the amount of the ethylcellulose coat surrounding the compressed core is about 9% w/w of the compressed core.

In one aspect, provided herein is a sustained release tablet comprising:

(a) a compressed core, said compressed core comprising 4-aminopyridine, a polyethylene oxide with a molecular weight between about 1,000,000 and 10,000,000, and a mixture comprising polyvinyl acetate and polyvinyl pyrrolidone; and (b) an amount of an ethylcellulose coat surrounding said compressed core, said amount of the ethylcellulose coat being in the range of about 5% w/w to about 7% w/w of the compressed core.

In one embodiment of the sustained release tablet provided herein, the amount of 4-aminopyridine is in the range of about 3% w/w to about 5% w/w of the compressed core and the amount of the ethylcellulose coat surrounding the compressed core is about 6% w/w of the compressed core.

In one aspect, provided herein is a sustained release tablet comprising:

(a) a compressed core, wherein said compressed core comprises: (i) 4-aminopyridine, (ii) a polyethylene oxide with a molecular weight between about 1,000,000 and 10,000,000, (iii) a mixture consisting of about 80% polyvinyl acetate, about 19% polyvinyl pyrrolidone, about 0.8% sodium lauryl sulfate, and about 0.2% of silica, (iv) dibasic calcium phosphate dihydrate, and (v) magnesium stearate; and (b) an amount of an ethylcellulose coat surrounding said compressed core, said amount of the ethylcellulose coat being in the range of about 8% w/w to about 10% w/w of the tablet, wherein said sustained release tablet is the product of a process comprising a curing step after coating the compressed core with ethylcellulose, wherein said curing step comprises exposing the coated compressed core to a temperature in the range of 50-60° C. for a period of time of at least 1 hour, and wherein the amount of 4-aminopyridine is in the range of about 4% w/w to about 6% w/w of the sustained release tablet.

In one embodiment, the polyethylene oxide in the sustained release tablet provided herein has a molecular weight between 4,000,000 and 8,000,000.

In one embodiment, the polyethylene oxide in the sustained release tablet provided herein has a molecular weight of 7,000,000.

In one embodiment, the total amount of the 4-aminopyridine in the tablet provided herein is in the range of about 1% w/w to about 10% w/w of the sustained release tablet.

In one embodiment, the total amount of the 4-aminopyridine in the tablet provided herein is in the range of about 1% w/w to about 10% w/w of the compressed core.

In one embodiment of the sustained release tablet provided herein, the amount of 4-aminopyridine in the compressed core is in the range of about 12 mg to about 25 mg.

In one embodiment of the sustained release tablet provided herein, the amount of 4-aminopyridine in the compressed core is in the range of about 20 mg to about 25 mg.

In one embodiment of the sustained release tablet provided herein, the amount of 4-aminopyridine in the compressed core is about 22 mg.

In one embodiment of the sustained release tablet provided herein, the amount of 4-aminopyridine in the compressed core is about 16.5 mg.

In one embodiment of the sustained release tablet provided herein, the amount of 4-aminopyridine in the compressed core is in the range of about 5 mg to about 12 mg.

In one aspect, provided herein is a sustained release tablet comprising:

(a) a compressed core, wherein said compressed core comprises: (i) 4-aminopyridine, wherein the amount of 4-aminopyridine is in the range of about 4% w/w to about 6% w/w of the compressed core; (ii) a polyethylene oxide with a molecular weight between about 1,000,000 and 10,000,000, wherein the amount of the polyethylene oxide is in the range of about 10% w/w to about 20% w/w of the compressed core; (iii) a mixture consisting of about 80% polyvinyl acetate, about 19% polyvinyl pyrrolidone, about 0.8% sodium lauryl sulfate, and about 0.2% of silica, wherein the amount of the mixture is in the range of about 20% w/w to about 30% w/w of the compressed core; (iv) dibasic calcium phosphate dihydrate, wherein the amount of dibasic calcium phosphate dihydrate is in the range of about 50% w/w to about 60% w/w of the compressed core; and (v) magnesium stearate, wherein the amount of magnesium stearate is in the range of about 0.7% w/w to about 1.3% w/w of the compressed core; and (b) an amount of an ethylcellulose coat surrounding said compressed core, said amount of the ethylcellulose coat being in the range of about 5% w/w to about 10% w/w of the compressed core.

In one aspect, provided herein is a sustained release tablet comprising:

(a) a compressed core, wherein said compressed core comprises: (i) 4-aminopyridine, wherein the amount of 4-aminopyridine is in the range of about 4% w/w to about 6% w/w of the compressed core; (ii) a polyethylene oxide with a molecular weight of 7,000,000, wherein the amount of the polyethylene oxide is about 15% w/w of the compressed core; (iii) a mixture consisting of about 80% polyvinyl acetate, about 19% polyvinyl pyrrolidone, about 0.8% sodium lauryl sulfate, and about 0.2% of silica, wherein the amount of the mixture is about 25% w/w of the compressed core; (iv) dibasic calcium phosphate dihydrate, wherein the amount of dibasic calcium phosphate dihydrate is about 54% w/w of the compressed core; and (v) magnesium stearate, wherein the amount of magnesium stearate is about 1% w/w of the compressed core; and (b) an amount of an ethylcellulose coat surrounding said compressed core, said amount of the ethylcellulose coat being about 9% w/w of the compressed core.

In one embodiment of the foregoing, the amount of 4-aminopyridine in the compressed core is about 22 mg.

In one aspect, provided herein is a sustained release tablet comprising:

(a) a compressed core, wherein said compressed core comprises: (i) 4-aminopyridine, wherein the amount of 4-aminopyridine is in the range of about 3% w/w to about 5% w/w of the compressed core; (ii) a polyethylene oxide with a molecular weight between about 1,000,000 and 10,000,000, wherein the amount of the polyethylene oxide is in the range of about 10% w/w to about 20% w/w of the compressed core; (iii) a mixture consisting of about 80% polyvinyl acetate, about 19% polyvinyl pyrrolidone, about 0.8% sodium lauryl sulfate, and about 0.2% of silica, wherein the amount of the mixture is in the range of about 20% w/w to about 30% w/w of the compressed core; (iv) dibasic calcium phosphate dihydrate, wherein the amount of dibasic calcium phosphate dihydrate is in the range of about 50% w/w to about 60% w/w of the compressed core; and (v) magnesium stearate, wherein the amount of magnesium stearate is in the range of about 0.7% w/w to about 1.3% w/w of the compressed core; and (b) an amount of an ethylcellulose coat surrounding said compressed core, said amount of the ethylcellulose coat being in the range of about 5% w/w to about 7% w/w of the compressed core.

In one aspect, provided herein is a sustained release tablet comprising:

(a) a compressed core, wherein said compressed core comprises: (i) 4-aminopyridine, wherein the amount of 4-aminopyridine is in the range of about 3% w/w to about 5% w/w of the compressed core; (ii) a polyethylene oxide with a molecular weight of 7,000,000, wherein the amount of the polyethylene oxide is about 15% w/w of the compressed core; (iii) a mixture consisting of about 80% polyvinyl acetate, about 19% polyvinyl pyrrolidone, about 0.8% sodium lauryl sulfate, and about 0.2% of silica, wherein the amount of the mixture is about 25% w/w of the compressed core; (iv) dibasic calcium phosphate dihydrate, wherein the amount of dibasic calcium phosphate dihydrate is about 55% w/w of the compressed core; and (v) magnesium stearate, wherein the amount of magnesium stearate is about 1% w/w of the compressed core; and (b) an amount of an ethylcellulose coat surrounding said compressed core, said amount of the ethylcellulose coat being about 6% w/w of the compressed core.

In one embodiment of the foregoing, the amount of 4-aminopyridine in the compressed core is about 16.5 mg.

In one embodiment, the sustained release tablet provided herein does not further comprise an immediate release drug overcoat containing 4-aminopyridine.

In one embodiment, the sustained release tablet provided herein provides a zero-order or near-zero-order release of the 4-aminopyridine. In one embodiment, the release is zero-order.

In one embodiment, the sustained release tablet provided herein is suitable for once daily oral administration.

In one embodiment, the sustained release tablet provided herein comprises an amount of 4-aminopyridine that is therapeutically effective over a period of 24 hours upon oral administration to a human patient.

In one embodiment, the release of the 4-aminopyridine from the sustained release tablet provided herein, upon subjecting the tablet to an in vitro dissolution test employing 50 mM Phosphate Buffer, pH 6.8 as dissolution medium, is as follows:

within the first 2 hours after the start of the test at most 30% w/w of the total amount of the 4-aminopyridine contained in the sustained release tablet is released.

In one embodiment, the release of the 4-aminopyridine from the sustained release tablet provided herein, upon subjecting the tablet to an in vitro dissolution test employing 50 mM Phosphate Buffer, pH 6.8 as dissolution medium, is as follows:

(a) within the first 2 hours after the start of the test at most 30% w/w of the total amount of the 4-aminopyridine contained in the sustained release tablet is released, and (b) within the first 24 hours after the start of the test at least 80% w/w of the total amount of the 4-aminopyridine contained in the sustained release tablet is released.

In one embodiment, the release of the 4-aminopyridine from the sustained release tablet provided herein, upon subjecting the tablet to an in vitro dissolution test employing 50 mM Phosphate Buffer, pH 6.8 as dissolution medium, is as follows:

within the first 2 hours after the start of the test at most 20% w/w of the total amount of the 4-aminopyridine contained in the sustained release tablet is released.

In one embodiment, the release of the 4-aminopyridine from the sustained release tablet provided herein, upon subjecting the tablet to an in vitro dissolution test employing 50 mM Phosphate Buffer, pH 6.8 as dissolution medium, is as follows:

(a) within the first 2 hours after the start of the test at most 20% w/w of the total amount of the 4-aminopyridine contained in the sustained release tablet is released, and (b) within the first 24 hours after the start of the test at least 80% w/w of the total amount of the 4-aminopyridine contained in the sustained release tablet is released.

In one embodiment, the sustained release tablet provided herein further comprises an immediate release drug overcoat containing 4-aminopyridine.

Provided herein is a method of making a sustained release tablet comprising 4-aminopyridine, which method comprises:

(a) forming a compressed core comprising (i) 4-aminopyridine, (ii) a polyethylene oxide with a molecular weight between about 1,000,000 and 10,000,000, (iii) a mixture comprising polyvinyl acetate and polyvinyl pyrrolidone; (iv) dibasic calcium phosphate dihydrate, and (v) magnesium stearate;

(b) coating the compressed core with an amount of ethylcellulose to form a coated compressed core, said amount of the ethylcellulose coat being in the range of about 5% w/w to about 10% w/w of the compressed core; and (c) curing the coated compressed core by exposing it to a temperature in the range of 40-70° C. for a period of time of at least 1 hour.

Provided herein is a method of making a sustained release tablet comprising 4-aminopyridine, which method comprises:

(a) forming a compressed core comprising (i) 4-aminopyridine, (ii) a polyethylene oxide with a molecular weight between about 1,000,000 and 10,000,000, (iii) a mixture comprising polyvinyl acetate and polyvinyl pyrrolidone; (iv) dibasic calcium phosphate dihydrate, and (v) magnesium stearate;

(b) coating the compressed core with an amount of ethylcellulose to form a coated compressed core, said amount of the ethylcellulose coat being in the range of about 8% w/w to about 10% w/w of the sustained release tablet; and (c) curing the coated compressed core by exposing it to a temperature in the range of 40-70° C. for a period of time of at least 1 hour.

In one embodiment, forming the compressed core in the method of making provided herein comprises:

(a) blending the 4-aminopyridine, polyethylene oxide, the mixture comprising polyvinyl acetate and polyvinyl pyrrolidone, and dibasic calcium phosphate dihydrate to form a blended mixture;

(b) adding magnesium stearate to the blended mixture to form a new blend; and (c) compressing the new blend to form a compressed core.

In one embodiment of the method of making provided herein, the mixture comprising polyvinyl acetate and polyvinyl pyrrolidone consists of about 80% polyvinyl acetate, about 19% polyvinyl pyrrolidone, about 0.8% sodium lauryl sulfate, and about 0.2% silica.

In one embodiment of the method of making provided herein, the polyethylene oxide has a molecular weight between 4,000,000 and 8,000,000. In one embodiment, the polyethylene oxide has a molecular weight of 7,000,000.

In one embodiment of the method of making provided herein, the coating comprises applying an aqueous ethylcellulose dispersion to the compressed core.

In one embodiment of the method of making provided herein, the total amount of the 4-aminopyridine in the sustained release tablet is in the range of about 1% w/w to about 10% w/w of the compressed core.

In one embodiment of the method of making provided herein, the total amount of the 4-aminopyridine in the sustained release tablet is in the range of about 1% w/w to about 10% w/w of the sustained release tablet.

Provided herein is a method of making a sustained release tablet comprising 4-aminopyridine, which method comprises:

(a) forming a compressed core comprising (i) 4-aminopyridine, wherein the amount of 4-aminopyridine is in the range of about 4% w/w to about 6% w/w of the compressed core, (ii) a polyethylene oxide with a molecular weight of 7,000,000, wherein the amount of the polyethylene oxide is about 15% w/w of the compressed core, (iii) a mixture consisting of about 80% polyvinyl acetate, about 19% polyvinyl pyrrolidone, about 0.8% sodium lauryl sulfate, and about 0.2% of silica, wherein the amount of the mixture is about 25% w/w of the compressed core; (iv) dibasic calcium phosphate dihydrate, wherein the amount of dibasic calcium phosphate dihydrate is about 54% w/w of the compressed core; and (v) magnesium stearate, wherein the amount of magnesium stearate is about 1% w/w of the compressed core;

(b) coating the compressed core with an amount of ethylcellulose to form a coated compressed core, said amount of the ethylcellulose coat being about 9% w/w of the compressed core; and (c) curing the coated compressed core by exposing it to a temperature in the range of 50-60° C. for a period of time of at least 1 hour.

In one embodiment of the foregoing method of making, the amount of 4-aminopyridine in the compressed core is about 22 mg.

Provided herein is a method of making a sustained release tablet comprising 4-aminopyridine, which method comprises:

(a) forming a compressed core comprising (i) 4-aminopyridine, wherein the amount of 4-aminopyridine is in the range of about 3% w/w to about 5% w/w of the compressed core, (ii) a polyethylene oxide with a molecular weight of 7,000,000, wherein the amount of the polyethylene oxide is about 15% w/w of the compressed core, (iii) a mixture consisting of about 80% polyvinyl acetate, about 19% polyvinyl pyrrolidone, about 0.8% sodium lauryl sulfate, and about 0.2% of silica, wherein the amount of the mixture is about 25% w/w of the compressed core; (iv) dibasic calcium phosphate dihydrate, wherein the amount of dibasic calcium phosphate dihydrate is about 55% w/w of the compressed core; and (v) magnesium stearate, wherein the amount of magnesium stearate is about 1% w/w of the compressed core;

(b) coating the compressed core with an amount of ethylcellulose to form a coated compressed core, said amount of the ethylcellulose coat being about 6% w/w of the compressed core; and (c) curing the coated compressed core by exposing it to a temperature in the range of 50-60° C. for a period of time of at least 1 hour.

In one embodiment of the foregoing method of making, the amount of 4-aminopyridine in the compressed core is about 16.5 mg.

In one embodiment of the method of making provided herein, the sustained release tablet is suitable for once daily oral administration.

In one embodiment of the method of making provided herein, the sustained release tablet comprises an amount of 4-aminopyridine that is therapeutically effective over a period of 24 hours.

Provided herein is a method of treating a neurological disorder in a patient in need thereof comprising orally administering to the patient once daily the sustained release tablet provided herein.

Provided herein is a method of treating a neurological disorder in a patient in need thereof comprising orally administering to the patient a therapeutically effective amount of the sustained release tablet provided herein, in combination with one or more additional medicaments. In one embodiment of the method of treating provided herein, the neurological disorder is multiple sclerosis, and the one or more additional medicaments is a therapeutic agent effective for the treatment of multiple sclerosis. In one embodiment, the one or more therapeutic agents effective for the treatment of multiple sclerosis is selected from the group consisting of interferon beta-1a, interferon beta-1b, glatiramer acetate, mitoxantrone, natalizumab, teriflunomide, fingolimod, alemtuzumab, peginterferon beta-1a, dimethyl fumarate, prednisone, prednisolone, methylprednisolone, betamethasone, and dexamethasone.

In one embodiment of the method of treating provided herein, the neurological disorder is multiple sclerosis or stroke.

In one embodiment of the method of treating provided herein, the neurological disorder is multiple sclerosis.

In one embodiment of the method of treating provided herein, the neurological disorder is a walking impairment associated with multiple sclerosis.

In one embodiment of the method of treating provided herein, the neurological disorder is a neurocognitive or neuropsychiatric impairment associated with multiple sclerosis.

In one embodiment of the method of treating provided herein, the neurological disorder is stroke.

In one embodiment of the method of treating provided herein, the neurological disorder is a sensorimotor impairment associated with stroke.

In one embodiment of the method of treating provided herein, the neurological disorder is a walking impairment associated with stroke.

In one embodiment of the method of treating provided herein, the patient is a human patient.

4 BRIEF DESCRIPTION OF THE FIGURES

Figure 3:
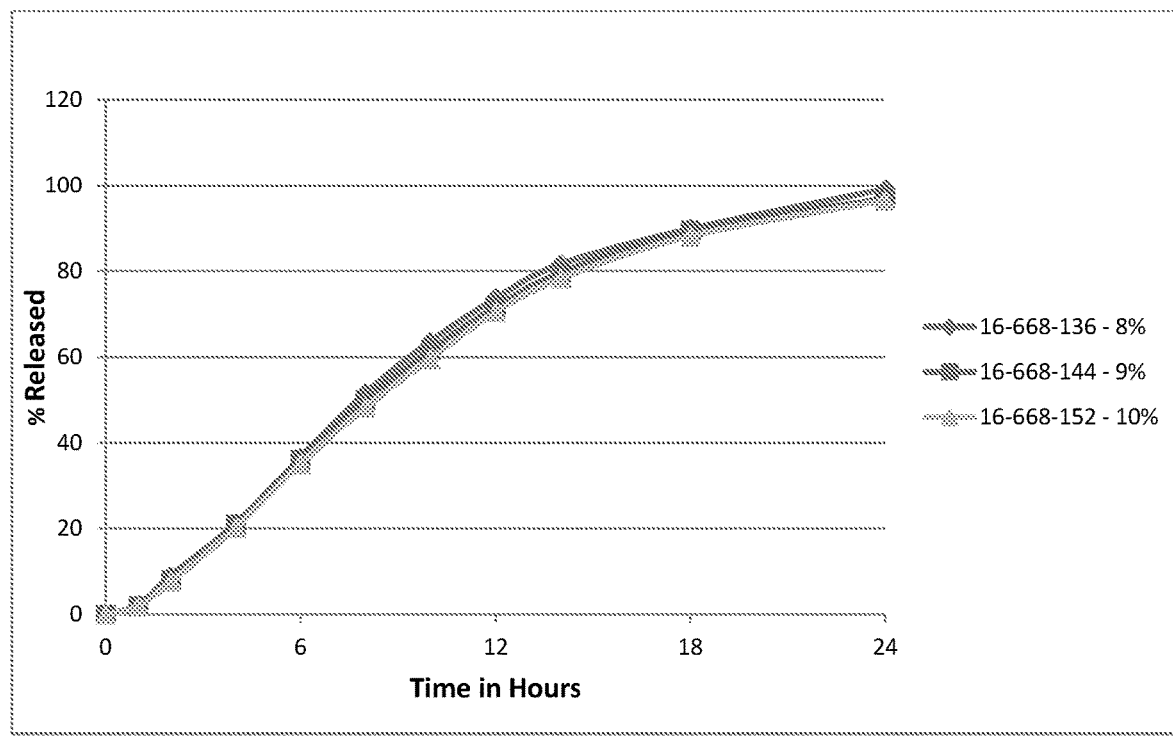

FIG. 3 depicts dissolution profiles of sustained release tablets containing 22 mg 4-aminopyridine, coated to 8%, 9%, and 10% weight gain, employing 50 mM Phosphate Buffer, pH 6.8 as a dissolution medium.

Figure 4:
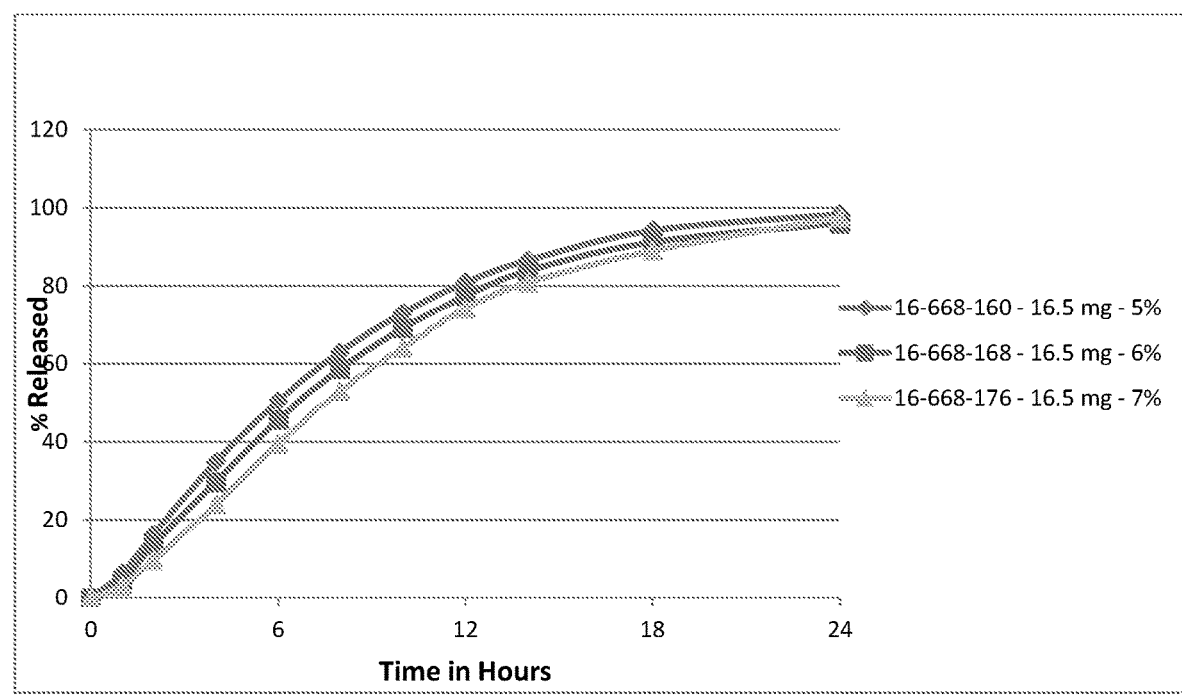

FIG. 4 depicts dissolution profiles of sustained release tablets containing 16.5 mg 4-aminopyridine, coated to 5%, 6%, and 7% weight gain, employing 50 mM Phosphate Buffer, pH 6.8 as a dissolution medium.

Figure 5:
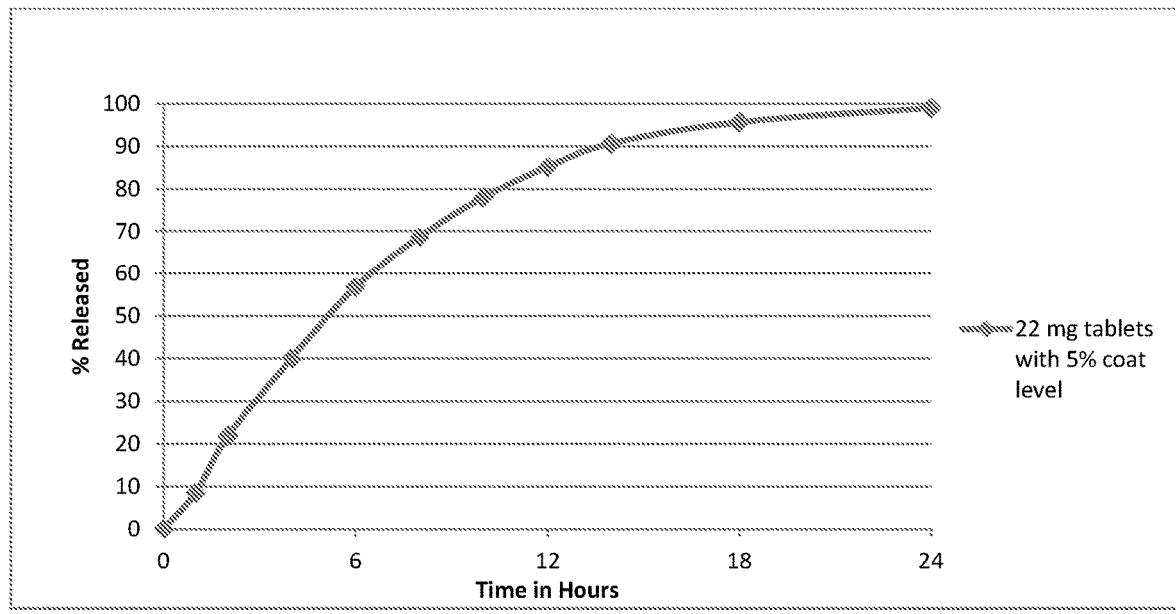

FIG. 5 depicts a dissolution profile of the sustained release tablet in Example 4 employing 50 mM Phosphate Buffer, pH 6.8 as a dissolution medium.

Figure 6:
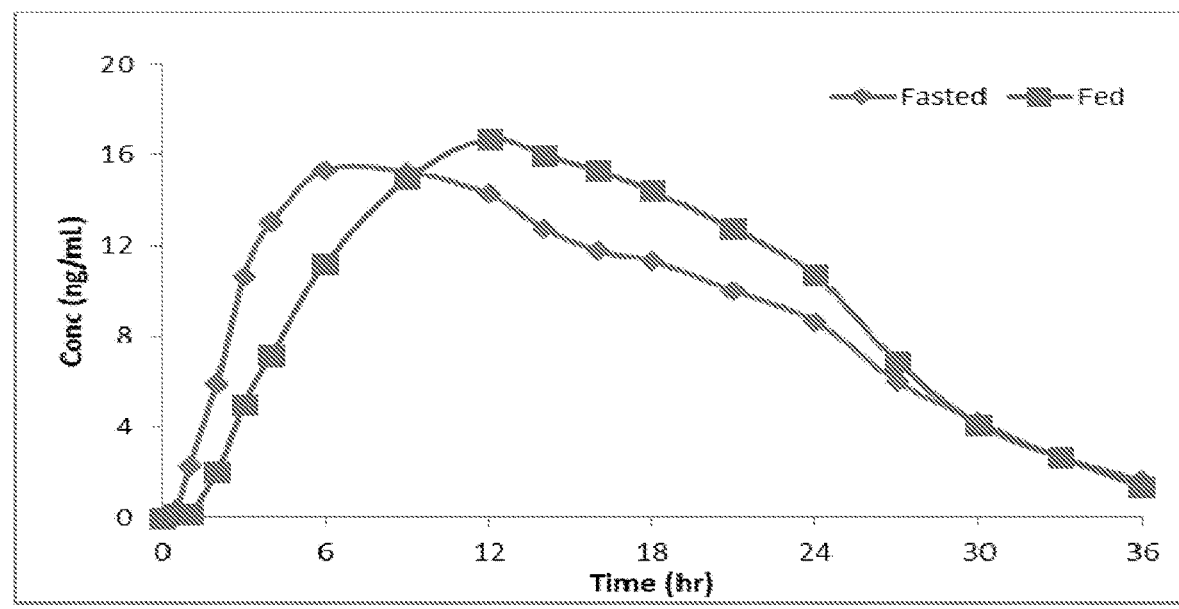

FIG. 6 depicts mean plasma levels following administration of a single oral dose of the 22 mg 4-aminopyridine sustained release tablet of Example 1 in human subjects in fed and fasted states.

5 DETAILED DESCRIPTION

5.1 Sustained Release Tablets

The invention provides sustained release tablets comprising 4-aminopyridine as the active ingredient, preferably for once daily administration.

Provided herein are sustained release tablets comprising: (a) a compressed core, said compressed core comprising 4-aminopyridine, a polyethylene oxide with a molecular weight between about 1,000,000 and 10,000,000, and a mixture comprising polyvinyl acetate and polyvinyl pyrrolidone; and (b) an amount of an ethylcellulose coat surrounding said compressed core, wherein the ratio of the amount of the ethylcellulose coat to the amount of 4-aminopyridine in the compressed core is in the range of about 0.5:1 to about 3:1; wherein for calculating said ratio, the amount of the ethylcellulose coat is the weight percentage of the ethylcellulose coat by weight of the compressed core, and the amount of 4-aminopyridine is the weight percentage of 4-aminopyridine by weight of the compressed core. In a specific embodiment of the foregoing, the sustained release tablet is the product of a process comprising a curing step after coating the compressed core with ethylcellulose, and wherein said curing step comprises heating the coated compressed core to a temperature above 23° C. for a period of time of at least 15 minutes.

Also provided herein are sustained release tablets comprising: (a) a compressed core, said compressed core comprising 4-aminopyridine, a polyethylene oxide with a molecular weight between about 1,000,000 and 10,000,000, and a mixture comprising polyvinyl acetate and polyvinyl pyrrolidone; and (b) an amount of an ethylcellulose coat surrounding said compressed core, wherein the ratio of the amount of the ethylcellulose coat to the amount of 4-aminopyridine in the compressed core is in the range of about 0.1:1 to about 0.7:1; wherein for calculating said ratio, the amount of the ethylcellulose coat is the weight percentage of the ethylcellulose coat by weight of the compressed core, and the amount of 4-aminopyridine is the weight in milligrams of 4-aminopyridine. In a specific embodiment of the foregoing, the sustained release tablet is the product of a process comprising a curing step after coating the compressed core with ethylcellulose, and wherein said curing step comprises heating the coated compressed core to a temperature above 23° C. for a period of time of at least 15 minutes.

Also provided herein are sustained release tablets comprising: (a) a compressed core, said compressed core comprising 4-aminopyridine, a polyethylene oxide with a molecular weight between about 1,000,000 and 10,000,000, and a mixture comprising polyvinyl acetate and polyvinyl pyrrolidone; and (b) an amount of an ethylcellulose coat surrounding said compressed core, said amount of the ethylcellulose coat being in the range of about 8% w/w to about 10% w/w of the tablet. In a specific embodiment of the foregoing, the sustained release tablet is the product of a process comprising a curing step after coating the compressed core with ethylcellulose, and wherein said curing step comprises heating the coated compressed core to a temperature above 23° C. for a period of time of at least 15 minutes.

Also provided herein are sustained release tablets comprising: (a) a compressed core, said compressed core comprising 4-aminopyridine, a polyethylene oxide with a molecular weight between about 1,000,000 and 10,000,000, and a mixture comprising polyvinyl acetate and polyvinyl pyrrolidone; and (b) an amount of an ethylcellulose coat surrounding said compressed core, said amount of the ethylcellulose coat being in the range of about 5% w/w to about 10% w/w of the compressed core. In a specific embodiment of the foregoing, the sustained release tablet is the product of a process comprising a curing step after coating the compressed core with ethylcellulose, and wherein said curing step comprises heating the coated compressed core to a temperature above 23° C. for a period of time of at least 15 minutes.

Also provided herein are sustained release tablets comprising:

(a) a compressed core, wherein said compressed core comprises (i) 4-aminopyridine, wherein the amount of 4-aminopyridine is in the range of about 4% w/w to about 6% w/w of the compressed core; (ii) a polyethylene oxide with a molecular weight of 7,000,000, wherein the amount of the polyethylene oxide is about 15% w/w of the compressed core; (iii) a mixture consisting of about 80% polyvinyl acetate, about 19% polyvinyl pyrrolidone, about 0.8% sodium lauryl sulfate, and about 0.2% of silica, wherein the amount of the mixture is about 25% w/w of the compressed core; (iv) dibasic calcium phosphate dihydrate, wherein the amount of dibasic calcium phosphate dihydrate is about 54% w/w of the compressed core; and (v) magnesium stearate, wherein the amount of magnesium stearate is about 1% w/w of the compressed core; and (b) an amount of an ethylcellulose coat surrounding said compressed core, said amount of the ethylcellulose coat being about 9% w/w of the compressed core.

In a specific embodiment of the foregoing embodiment, the amount of 4-aminopyridine in the compressed core is about 22 mg. In another specific embodiment of the foregoing, the sustained release tablet is the product of a process comprising a curing step after coating the compressed core with ethylcellulose, wherein said curing step comprises exposing the coated compressed core to a temperature in the range of 50-60° C. for a period of time of at least 1 hour.

Also provided herein are sustained release tablets comprising:

(a) a compressed core, wherein said compressed core comprises (i) 4-aminopyridine, wherein the amount of 4-aminopyridine is in the range of about 4% w/w to about 6% w/w of the compressed core; (ii) a polyethylene oxide with a molecular weight of 7,000,000, wherein the amount of the polyethylene oxide is about 15% w/w of the compressed core; (iii) a mixture consisting of about 80% polyvinyl acetate, about 19% polyvinyl pyrrolidone, about 0.8% sodium lauryl sulfate, and about 0.2% of silica, wherein the amount of the mixture is about 25% w/w of the compressed core; (iv) dibasic calcium phosphate dihydrate, wherein the amount of dibasic calcium phosphate dihydrate is about 54% w/w of the compressed core; and (v) magnesium stearate, wherein the amount of magnesium stearate is about 1% w/w of the compressed core; and (b) an amount of an ethylcellulose coat surrounding said compressed core, said amount of the ethylcellulose coat being about 5% w/w of the compressed core.

In a specific embodiment of the foregoing embodiment, the amount of 4-aminopyridine in the compressed core is about 22 mg. In another specific embodiment of the foregoing, the sustained release tablet is the product of a process comprising a curing step after coating the compressed core with ethylcellulose, wherein said curing step comprises exposing the coated compressed core to a temperature in the range of 50-60° C. for a period of time of at least 1 hour.

Also provided herein are sustained release tablets comprising: (a) a compressed core, said compressed core comprising 4-aminopyridine, a polyethylene oxide with a molecular weight between about 1,000,000 and 10,000,000, and a mixture comprising polyvinyl acetate and polyvinyl pyrrolidone; and (b) an amount of an ethylcellulose coat surrounding said compressed core, said amount of the ethylcellulose coat being in the range of about 5% w/w to about 7% w/w of the compressed core. In a specific embodiment of the foregoing, the sustained release tablet is the product of a process comprising a curing step after coating the compressed core with ethylcellulose, and wherein said curing step comprises heating the coated compressed core to a temperature above 23° C. for a period of time of at least 15 minutes.

Also provided herein are sustained release tablets comprising:

(a) a compressed core, wherein said compressed core comprises (i) 4-aminopyridine, wherein the amount of 4-aminopyridine is in the range of about 3% w/w to about 5% w/w of the compressed core; (ii) a polyethylene oxide with a molecular weight of 7,000,000, wherein the amount of the polyethylene oxide is about 15% w/w of the compressed core; (iii) a mixture consisting of about 80% polyvinyl acetate, about 19% polyvinyl pyrrolidone, about 0.8% sodium lauryl sulfate, and about 0.2% of silica, wherein the amount of the mixture is about 25% w/w of the compressed core; (iv) dibasic calcium phosphate dihydrate, wherein the amount of dibasic calcium phosphate dihydrate is about 55% w/w of the compressed core; and (v) magnesium stearate, wherein the amount of magnesium stearate is about 1% w/w of the compressed core; and (b) an amount of an ethylcellulose coat surrounding said compressed core, said amount of the ethylcellulose coat being about 6% w/w of the compressed core.

In a specific embodiment of the foregoing embodiment, the amount of 4-aminopyridine in the compressed core is about 16.5 mg. In another specific embodiment of the foregoing, the sustained release tablet is the product of a process comprising a curing step after coating the compressed core with ethylcellulose, wherein said curing step comprises exposing the coated compressed core to a temperature in the range of 50-60° C. for a period of time of at least 1 hour.

In specific embodiments, the sustained release tablets comprise, or consist essentially of, or consist of, the components as described herein. The sustained release tablets are pharmaceutically acceptable. The terms "sustained release" and "extended release" as used herein are generally synonymous unless the context clearly indicates otherwise.

In a specific embodiment, the compressed core provided herein comprises 4-aminopyridine, a polyethylene oxide with a molecular weight between about 1,000,000 and 10,000,000, and a mixture comprising polyvinyl acetate and polyvinyl pyrrolidone. In a specific embodiment, the compressed core provided herein consists essentially of 4-aminopyridine, a polyethylene oxide with a molecular weight between about 1,000,000 and 10,000,000, and a mixture comprising polyvinyl acetate and polyvinyl pyrrolidone. In a specific embodiment, the mixture consists essentially of polyvinyl acetate and polyvinyl pyrrolidone, and optionally a surfactant and optionally silica.

In a specific embodiment, the amount of 4-aminopyridine in the sustained release tablet is in the range of about 1% w/w to about 10% w/w of the sustained release tablet. In some embodiments, the amount of 4-aminopyridine in the sustained release tablet is in range of about 1% w/w to about 7% w/w, about 1% w/w to about 5% w/w, about 1% w/w to about 3% w/w, about 1% w/w to about 2% w/w, about 2% w/w to about 10% w/w, about 2% w/w to about 7% w/w, about 2% w/w to about 5% w/w, about 2% w/w to about 3% w/w, about 3% w/w to about 10% w/w, about 3% w/w to about 7% w/w, about 3% w/w to about 5% w/w, about 3% w/w to about 4% w/w, about 4% w/w to about 10% w/w, about 4% w/w to about 7% w/w, about 4% w/w to about 6% w/w, about 4% w/w to about 5% w/w, about 5% w/w to about 10% w/w, about 5% w/w to about 7% w/w, about 5% w/w to about 6% w/w, 7% w/w to about 10% w/w, about 7% w/w to about 8% w/w, about 7% w/w to about 9% w/w, about 8% w/w to about 10% w/w, about 8% w/w to about 9% w/w, or about 9% w/w to about 10% w/w of the sustained release tablet.

In a specific embodiment, the amount of 4-aminopyridine in the compressed core is in the range of about 1% w/w to about 10% w/w of the compressed core. In some embodiments, the amount of 4-aminopyridine in the compressed core is in range of about 1% w/w to about 7% w/w, about 1% w/w to about 5% w/w, about 1% w/w to about 3% w/w, about 1% w/w to about 2% w/w, about 2% w/w to about 10% w/w, about 2% w/w to about 7% w/w, about 2% w/w to about 5% w/w, about 2% w/w to about 3% w/w, about 3% w/w to about 10% w/w, about 3% w/w to about 7% w/w, about 3% w/w to about 5% w/w, about 3% w/w to about 4% w/w, about 4% w/w to about 10% w/w, about 4% w/w to about 7% w/w, about 4% w/w to about 6% w/w, about 4% w/w to about 5% w/w, about 5% w/w to about 10% w/w, about 5% w/w to about 7% w/w, about 5% w/w to about 6% w/w, 7% w/w to about 10% w/w, about 7% w/w to about 8% w/w, about 7% w/w to about 9% w/w, about 8% w/w to about 10% w/w, about 8% w/w to about 9% w/w, or about 9% w/w to about 10% w/w of the compressed core. In some embodiments, the amount of 4-aminopyridine in the compressed core is about 2% w/w, about 2.25% w/w, about 2.5% w/w, about 2.75% w/w, about 3% w/w, about 3.25% w/w, about 3.5% w/w, about 3.75% w/w, about 4% w/w, about 4.25% w/w, about 4.5% w/w, about 4.75% w/w, or about 5% w/w of the compressed core. In a specific embodiment, the amount of 4-aminopyridine in the compressed core is in the range of about 3% w/w to about 5% of the compressed core. In another specific embodiment, the amount of 4-aminopyridine in the compressed core is in the range of about 4% w/w to about 6% w/w of the compressed core. In a specific embodiment, the amount of 4-aminopyridine in the compressed core is about 2.5% w/w of the compressed core. In a specific embodiment, the amount of 4-aminopyridine in the compressed core is about 3.75% w/w of the compressed core. In a specific embodiment, the amount of 4-aminopyridine in the compressed core is about 5% w/w of the compressed core.

In some embodiments, the amount of 4-aminopyridine in the compressed core is in the range of about 5 mg to about 40 mg. In some embodiments, the amount of 4-aminopyridine in the compressed core is in the range of about 5 mg to about 35 mg, about 5 mg to about 30 mg, about 5 mg to about 25 mg, about 5 mg to about 20 mg, about 5 mg to about 15 mg, about 5 mg to about 10 mg, about 10 mg to about 40 mg, about 10 mg to about 35 mg, about 10 mg to about 30 mg, about 10 mg to about 25 mg, about 10 mg to about 20 mg, about 10 mg to about 15 mg, about 15 mg to about 40 mg, about 15 mg to about 35 mg, about 15 mg to about 30 mg, about 15 mg to about 25 mg, about 15 mg to about 20 mg, about 20 mg to about 40 mg, about 20 mg to about 35 mg, about 20 mg to about 30 mg, about 20 mg to about 25 mg, about 25 mg to about 40 mg, about 25 mg to about 35 mg, about 25 mg to about 30 mg, about 30 mg to about 40 mg, about 30 mg to about 35 mg, or about 35 mg to about 40 mg. In a specific embodiment, the amount of 4-aminopyridine in the compressed core is about 16 mg, about 16.2 mg, about 16.4 mg, about 16.6 mg, about 16.8 mg, about 17 mg, about 17.2 mg, about 17.4 mg, about 17.6 mg, about 17.8 mg, about 18 mg, about 18.2 mg, about 18.4 mg, about 18.6 mg, about 18.8 mg, about 19 mg, about 19.2 mg, about 19.4 mg, about 19.6 mg, about 19.8 mg, about 20 mg, about 20.2 mg, about 20.4 mg, about 20.6 mg, about 20.8 mg, about 21 mg, about 21.2 mg, about 21.4 mg, about 21.6 mg, about 21.8 mg, about 22 mg, about 22.2 mg, about 22.4 mg, about 22.6 mg, about 22.8 mg, about 23 mg, about 23.2 mg, about 23.4 mg, about 23.6 mg, about 23.8 mg, about 24 mg, about 24.2 mg, about 24.4 mg, about 24.6 mg, about 24.8 mg, or about 25 mg. In one embodiment, the amount of 4-aminopyridine in the compressed core is in the range of about 12 mg to about 40 mg. In one embodiment, the amount of 4-aminopyridine in the compressed core is in the range of about 12 mg to about 25 mg. In one embodiment, the amount of 4-aminopyridine in the compressed core is in the range of about 12 mg to about 15 mg. In one embodiment, the amount of 4-aminopyridine in the compressed core is in the range of about 5 mg to about 12 mg. In a specific embodiment, the amount of 4-aminopyridine in the compressed core is about 22 mg. In another specific embodiment, the amount of 4-aminopyridine in the compressed core is about 16.5 mg. In another specific embodiment, the amount of 4-aminopyridine in the compressed core is about 11 mg. In a preferred embodiment, 4-aminopyridine is present only in the compressed core (and thus the sustained release tablet does not have an immediate-release drug overcoat containing 4-aminopyridine). In an alternative specific embodiment, 4-aminopyridine is present only in: the compressed core and in an immediate-release drug overcoat of the sustained release tablet.

In a specific embodiment, the amount of 4-aminopyridine in the compressed core is about 5% w/w of the compressed core, said amount being equal to about 22 mg. In another specific embodiment, the amount of 4-aminopyridine in the sustained release tablet is about 3.75% w/w of the compressed core, said amount being equal to about 16.5 mg.

The sustained release tablet provided herein comprises one or more polymers that are capable of modifying the release rate of the 4-aminopyridine from the sustained release tablet. Examples of such release modifying polymers include, but are not limited to, polyethylene oxide, a mixture of polyvinyl acetate and polyvinyl pyrrolidone (e.g., KOLLIDON® SR), hypromellose, ethylcellulose, povidone, and any combination thereof. In one embodiment, the sustained release tablet comprises polyethylene oxide and a mixture of polyvinyl acetate and polyvinyl pyrrolidone (e.g., KOLLIDON® SR).

Polyethylene oxide is a hydrophilic, water soluble polymer with good binding, thickening, lubricity, water retention, and film forming properties. Polyethylene oxide also has beneficial effects in retarding the release rate of a drug from a suitable pharmaceutical composition. In a specific embodiment, the polyethylene oxide present in the sustained release tablet disclosed herein has a molecular weight between 4,000,000 and 8,000,000. In another specific embodiment, the polyethylene oxide has a molecular weight of 7,000,000. In another specific embodiment, the polyethylene oxide is sold under the name POLYOX WSR-303 available from Dow Chemical Co.

In some embodiments, the amount of the polyethylene oxide in the compressed core is in the range of about 5% w/w to about 25% w/w of the compressed core. In some embodiments, the amount of the polyethylene oxide in the compressed core is in the range of about 5% w/w to about 20% w/w, about 5% w/w to about 15% w/w, about 5% w/w to about 10% w/w, about 10% w/w to about 25% w/w, 10% w/w to about 20% w/w, about 10% w/w to about 15% w/w, about 12% w/w to about 25% w/w, about 12% w/w to about 20% w/w, about 12% w/w to about 15% w/w, about 15% w/w to about 25% w/w, 15% w/w to about 20% w/w, or about 20% w/w to about 25% w/w of the compressed core. In a specific embodiment, the amount of the polyethylene oxide in the compressed core is about 10% w/w, about 10.5% w/w, about 11% w/w, about 11.5% w/w, about 12.5% w/w, about 13% w/w, about 13.5% w/w, about 14% w/w, about 14.5% w/w, about 15% w/w, about 15.5% w/w, about 16% w/w, about 16.5% w/w, or about 17% w/w of the compressed core. In a specific embodiment, the amount of the polyethylene oxide in the compressed core is in the range of about 10% w/w to about 20% w/w of the compressed core. In a specific embodiment, the amount of the polyethylene oxide in the compressed core is about 15% w/w of the compressed core. In another specific embodiment, the polyethylene oxide in the compressed core is a polyethylene oxide having a molecular weight of about 7,000,000, which is present in an amount of about 15% w/w of the compressed core.

In a specific embodiment, the mixture of polyvinyl acetate and polyvinyl pyrrolidone present in the sustained release tablet disclosed herein further comprises a surfactant. In a specific embodiment, the mixture further comprises silica. In another specific embodiment, the mixture further comprises a surfactant and silica. The surfactants suitable for use in the mixture provided herein include, but are not limited to, sodium lauryl sulfate, polyethylene stearates, polyethylene sorbitan fatty acid esters, polyoxyethylene castor oil derivatives, polyoxyethylene alkyl ethers, benzyl benzoate, cetrimide, cetyl alcohol, docusate sodium, glyceryl monooleate, glyceryl monostearate, glyceryl palmitostearate, lecithin, medium chain triglycerides, monoethanolamine, oleic acid, poloxamers, polyvinyl alcohol and sorbitan fatty acid esters. In a specific embodiment, the surfactant is sodium lauryl sulfate.

In specific embodiments, the mixture of polyvinyl acetate and polyvinyl pyrrolidone comprises 70-90% polyvinyl acetate and 15-20% polyvinyl pyrrolidone. In a specific embodiment, the mixture consists of about 80% polyvinyl acetate, about 19% polyvinyl pyrrolidone, about 0.8% sodium lauryl sulfate, and about 0.2% of silica. In one embodiment, the mixture comprising polyvinyl acetate and polyvinyl pyrrolidone is KOLLIDON® SR polyvinyl acetate/polyvinyl pyrrolidone (BASF); KOLLIDON® SR is a blend of 80% polyvinyl acetate and 19% povidone (also called polyvinyl pyrrolidone) along with small quantities of sodium lauryl sulfate and silica used as stabilizers (see Signet Chemical Corporation's website page for KOLLIDON® SR).

In some embodiments, the amount of the mixture comprising polyvinyl acetate and polyvinyl pyrrolidone in the compressed core is in the range of about 10% w/w to about 40% w/w of the compressed core.

In some embodiments, the amount of the mixture comprising polyvinyl acetate and polyvinyl pyrrolidone in the compressed core is in the range of about 10% w/w to about 35% w/w, about 10% w/w to about 30% w/w, about 10% w/w to about 25% w/w, about 10% w/w to about 20% w/w, about 10% w/w to about 15% w/w, about 15% w/w to about 40% w/w, about 15% w/w to about 35% w/w, about 15% w/w to about 30% w/w, about 15% w/w to about 25% w/w, about 15% w/w to about 20% w/w, about 20% w/w to about 40% w/w, about 20% w/w to about 35% w/w, about 20% w/w to about 30% w/w, about 20% w/w to about 25% w/w, about 25% w/w to about 40% w/w, about 25% w/w to about 35% w/w, about 25% w/w to about 30% w/w, about 30% w/w to about 40% w/w, about 30% w/w to about 35% w/w, or about 35% w/w to about 40% w/w of the compressed core. In a specific embodiment, the amount of the mixture comprising polyvinyl acetate and polyvinyl pyrrolidone in the compressed core is in the range of about 20% w/w to about 30% w/w. In some embodiments, the amount of the mixture comprising polyvinyl acetate and polyvinyl pyrrolidone in the compressed core is about 20% w/w, about 20.5% w/w, about 21% w/w, about 21.5% w/w, about 22% w/w, about 22.5% w/w, about 23% w/w, about 23.5% w/w, about 24% w/w, about 24.5% w/w, about 25% w/w, about 25.5% w/w, about 26% w/w, about 26.5% w/w, about 27% w/w, about 27.5% w/w, about 28% w/w, about 28.5% w/w, about 29% w/w, about 29.5% w/w, or about 30% w/w of the compressed core. In a specific embodiment, the amount of the mixture comprising polyvinyl acetate and polyvinyl pyrrolidone in the compressed core is about 25% w/w of the compressed core.

In addition to the polymers described herein, one or more fillers, binders, lubricants and the like may be used in the compressed core of the invention.

Suitable fillers include, as described in U.S. Pat. No. 8,858,993, but are not limited to, inorganic compounds such as the chloride, sulfate, and phosphate salts of potassium, sodium and magnesium as well as calcium citrate, phosphate, lactate, gluconate and succinate salts. In a specific embodiment, the filler is dibasic calcium phosphate dihydrate.

The concentration for the filler can be in the range of about 40% w/w to about 60% w/w of the sustained release tablet. In a specific embodiment, the amount of the filler in the compressed core is in the range of about 47% w/w to about 53% w/w of the sustained release tablet.

In some embodiments, the amount of the filler in the compressed core is in the range of about 40% w/w to about 65% w/w of the compressed core. In some embodiments, the amount of the filler in the compressed core is in the range of about 40% w/w to about 60% w/w about 40% w/w to about 55% w/w, about 40% w/w to about 50% w/w, about 40% w/w to about 45% w/w, about 45% w/w to about 65% w/w, about 45% w/w to about 60% w/w, about 45% w/w to about 55% w/w, about 45% w/w to about 50% w/w, about 50% w/w to about 65% w/w, about 50% w/w to about 60% w/w, about 50% w/w to about 55% w/w, about 55% w/w to about 65% w/w, about 55% w/w to about 60% w/w, or about 60% w/w to about 65% w/w of the compressed core. In a specific embodiment, the amount of the filler in the compressed core is in the range of about 50% w/w to about 60% w/w of the compressed core. In some embodiments, the amount of the filler in the compressed core is about 45% w/w, about 46% w/w, about 47% w/w, about 48% w/w, about 49% w/w, about 50% w/w, about 51% w/w, about 52% w/w, about 53% w/w, about 54% w/w, about 55% w/w, about 56% w/w, about 57% w/w, about 58% w/w, about 58% w/w, or about 60% w/w of the compressed core. In a specific embodiment, the amount of the filler in the compressed core is about 54% w/w of the compressed core. In another specific embodiment, the amount of the filler in the compressed core is about 55% w/w of the compressed core. In a specific embodiment, the filler is dibasic calcium phosphate dihydrate in an amount of about 54% w/w of the compressed core. In another specific embodiment, the filler is dibasic calcium phosphate dihydrate in an amount of about 55% w/w of the compressed core.

Pharmaceutically acceptable binders suitable for use in the compressed core of the present invention include, as described in U.S. Pat. No. 8,858,993, but are not limited to, sucrose, gelatin, acacia, tragacanth, cellulose derivatives, povidone, and other binders known to those familiar with pharmaceutical formulations.

The compressed core provided herein may further comprise one or more lubricants. Examples of lubricants include, but are not limited to, stearate salts; e.g., calcium stearate, magnesium stearate, zinc stearate, and sodium stearyl fumarate; stearic acid; mineral oil; vegetable oil derivatives; talc; and the like. In a specific embodiment, the lubricant is magnesium stearate.

The concentration ranges for lubricants can be up to about 5% by weight of the sustained release tablet. In general, lubricants are present at a concentration of 0.5-5% by weight of the sustained release tablet. In a specific embodiment, the amount of lubricant in the compressed core is in the range of about 0.7% w/w to about 1.3% w/w of the sustained release tablet. In some embodiments, the compressed core contains no lubricant.

In some embodiments, the amount of the lubricant in the compressed core is up to about 5% w/w of the compressed core. In some embodiments, the amount of lubricant in the compressed core is in the range of about 0.5% w/w to about 5% w/w of the compressed core. In a specific embodiment, the amount of lubricant in the compressed core is in the range of about 0.7% w/w to about 1.3% w/w of the compressed core. In a specific embodiment, the amount of the lubricant in the compressed core is about 1% w/w of the compressed core. In a specific embodiment, the lubricant is magnesium stearate in an amount of about 1% w/w of the compressed core.

In specific embodiments, the core comprising the 4-aminopyridine, polyethylene oxide polymer, mixture of polyvinyl acetate and polyvinyl pyrrolidone, and optionally one or more fillers, binders and lubricants is compressed to form intermediate tablets by methods well known in the art. The compressed core as described herein refers to such intermediate tablets. The compressed core (i.e., the intermediate tablets) is coated with a coating agent, and the resulting coated tablets are subjected to a curing step by exposing the coated tablets to a thermal treatment to yield the final sustained release tablets.

The release profile of 4-aminopyridine from the tablet can be modulated by coating the compressed core (i.e., the intermediate tablet) with a suitable coating agent. In specific embodiments, the compressed core is coated with a solution of ethyl cellulose or other cellulosic materials. In specific embodiments, the compressed core is coated with a colloidal suspension or a dispersion of ethyl cellulose, optionally with additional components such as light silicic acid anhydrides. Such light silicic anhydrides are described in The Pharmacopoeia of Japan XII and are commercially available under the trade name of, for example, AEROSIL-200 (produced by Nippon Aerosil Co., Ltd.). In some embodiments, an ethyl ether of cellulose having an ethoxy group content of 46 to 51% is employed as a coating agent. This type of ethyl cellulose is commercially available under the trade name, for example, of ETHOCEL STANDARD (produced by Dow Chemical Co., Ltd.) and the like. In certain embodiments, the coating agent comprises a solution of ethyl cellulose in ethanol.

In a specific embodiment, the coating agent comprises pH independent ethylcellulose. A "pH independent" ethylcellulose provides for a pH independent release of the 4-aminopyridine from the tablet. In a specific embodiment, the coating agent is an aqueous ethylcellulose dispersion. In a specific embodiment, the coating agent is SURELEASE®, commercially available from Colorcon. SURELEASE® is a pH independent ethylcellulose provided as an aqueous ethylcellulose dispersion. Another aqueous ethylcellulose dispersion that can be used as the coating agent is AQUA-COAT® ECD Ethylcellulose Aqueous Dispersion, commercially available from FMC BioPolymer. As will be clear, the ethylcellulose coat can contain other compounds in addition to ethylcellulose, but ethylcellulose will be the predominant component by weight of the ethylcellulose coat. In a specific embodiment, the amount of the ethylcellulose coat surrounding the compressed core is 8-10% w/w of the final sustained release tablet.

In one embodiment, the amount of the ethylcellulose coat surrounding the compressed core is in the range of about 1% w/w to about 20% w/w of the compressed core. In a specific embodiment, the amount of the ethylcellulose coat surrounding the compressed core is in the range of about 5% w/w to about 10% w/w of the compressed core. In some embodiments, the amount of the ethylcellulose coat surrounding the compressed core is above 8% w/w and up to about 20% w/w of the compressed core. In a specific embodiment, the amount of the ethylcellulose coat surrounding the compressed core is above 8% w/w and up to about 12% w/w or above 8% w/w and up to about 10% w/w of the compressed core. In another specific embodiment, the amount of the ethylcellulose coat surrounding the compressed core is in the range of about 8% w/w to about 10% w/w of the compressed core. In some embodiments, the amount of the ethylcellulose coat surrounding the compressed core is in the range of about 8% w/w to about 9.5% w/w, about 8% w/w to about 9% w/w, 8% w/w to about 8.5% w/w, about 9% w/w to about 10% w/w, about 9% w/w to about 9.5% w/w, or about 9.5% w/w to about 10% w/w of the compressed core. In some embodiments, the amount of the ethylcellulose coat surrounding the compressed core is about 8% w/w, about 8.1% w/w, about 8.2% w/w, 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10% w/w of the compressed core. In a specific embodiment, the amount of the ethylcellulose coat surrounding the compressed core is about 8% w/w of the compressed core. In a specific embodiment, the amount of the ethylcellulose coat surrounding the compressed core is about 9% w/w of the compressed core. In a specific embodiment, the amount of the ethylcellulose coat surrounding the compressed core is about 10% w/w of the compressed core.

In some embodiments, the amount of the ethylcellulose coat surrounding the compressed core is in the range of about 5% w/w to about 8% w/w of the compressed core. In some embodiments, the amount of the ethylcellulose coat surrounding the compressed core is in the range of about 5% w/w to about 7% w/w of the compressed core. In some embodiments, the amount of the ethylcellulose coat surrounding the compressed core is in the range of about 5% w/w to about 7.5% w/w, about 5% w/w to about 7% w/w, about 5% w/w to about 6.5% w/w, about 5% w/w to about 6% w/w, 5% w/w to about 5.5% w/w, about 5.5% w/w to about 8% w/w, about 5.5% w/w to about 7.5% w/w, about 5.5% w/w to about 7% w/w, about 5.5% w/w to about 6.5% w/w, about 5.5% w/w to about 6% w/w, about 6% w/w to about 8% w/w, about 6% w/w to about 7.5% w/w, about 6% w/w to about 7% w/w, about 6.5% w/w to about 8% w/w, about 6.5% w/w to about 7.5% w/w, about 6.5% w/w to about 7% w/w, about 7% w/w to about 8% w/w, about 7% w/w to about 7.5% w/w, or about 7.5% w/w to about 8% w/w of the compressed core. In some embodiments, the amount of the ethylcellulose coat surrounding the compressed core is about 5% w/w, about 5.1% w/w, about 5.2% w/w, 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, or about 7% w/w of the compressed core. In a specific embodiment, the amount of the ethylcellulose coat surrounding the compressed core is about 5% w/w of the compressed core. In a specific embodiment, the amount of the ethylcellulose coat surrounding the compressed core is about 6% w/w of the compressed core. In a specific embodiment, the amount of the ethylcellulose coat surrounding the compressed core is about 7% w/w of the compressed core.

As will be clear, the amount of the ethylcellulose coat expressed in terms of % w/w of the compressed core is equivalent to the amount of the ethylcellulose coat expressed in terms of % weight gain. In other words, by way of example, if the weight of the compressed core is 100 mg, a 10% weight gain after coating the compressed core with the ethylcellulose coat is an amount of the ethylcellulose coat that is equal to 10% w/w of the compressed core, which is 10 mg.

In one embodiment, the amount of the ethylcellulose coat surrounding the compressed core is in the range of about 5% w/w to about 10% w/w of the compressed core, and the amount of 4-aminopyridine in the compressed core is in the range of about 4% w/w to about 6% w/w of the compressed core. In a specific embodiment, the amount of the ethylcellulose coat surrounding the compressed core is in the range of about 5% w/w to about 10% w/w of the compressed core, and the amount of 4-aminopyridine in the compressed core is about 22 mg. In another specific embodiment, the amount of the ethylcellulose coat surrounding the compressed core is about 5% w/w of the compressed core, and the amount of 4-aminopyridine in the compressed core is in the range of about 4% w/w to about 6% w/w of the compressed core. In another specific embodiment, the amount of the ethylcellulose coat surrounding the compressed core is about 5% w/w of the compressed core, and the amount of 4-aminopyridine in the compressed core is about 22 mg.

In a specific embodiment, the amount of the ethylcellulose coat surrounding the compressed core is in the range of about 8% w/w to about 10% w/w of the compressed core, and the amount of 4-aminopyridine in the compressed core is in the range of about 4% w/w to about 6% w/w of the compressed core. In another specific embodiment, the amount of the ethylcellulose coat surrounding the compressed core is in the range of about 8% w/w to about 10% w/w of the compressed core, and the amount of 4-aminopyridine in the compressed core is about 22 mg. In another specific embodiment, the amount of the ethylcellulose coat surrounding the compressed core is about 9% w/w of the compressed core, and the amount of 4-aminopyridine in the compressed core is in the range of about 4% w/w to about 6% w/w of the compressed core. In another specific embodiment, the amount of the ethylcellulose coat surrounding the compressed core is about 9% w/w of the compressed core, and the amount of 4-aminopyridine in the compressed core is about 22 mg.

In one embodiment, the amount of the ethylcellulose coat surrounding the compressed core is in the range of about 5% w/w to about 7% w/w of the compressed core, and the amount of 4-aminopyridine in the compressed core is in the range of about 3% w/w to about 5% w/w of the compressed core. In another embodiment, the amount of the ethylcellulose coat surrounding the compressed core is about 6% w/w of the compressed core, and the amount of 4-aminopyridine in the compressed core is in the range of about 3% w/w to about 5% w/w of the compressed core. In another specific embodiment, the amount of the ethylcellulose coat surrounding the compressed core is in the range of about 5% w/w to about 7% w/w of the compressed core, and the amount of 4-aminopyridine in the compressed core is about 16.5 mg.

In one embodiment, the amount of the ethylcellulose coat surrounding the compressed core is in the range of about 2% w/w to about 5% w/w of the compressed core, and the amount of 4-aminopyridine in the compressed core is about 16.5 mg. In another specific embodiment, the amount of the ethylcellulose coat surrounding the compressed core is about 3% w/w of the compressed core, and the amount of 4-aminopyridine in the compressed core is about 16.5 mg. In another specific embodiment, the amount of the ethylcellulose coat surrounding the compressed core is about 4% w/w of the compressed core, and the amount of 4-aminopyridine in the compressed core is about 16.5 mg. In another specific embodiment, the amount of the ethylcellulose coat surrounding the compressed core is about 5% w/w of the compressed core, and the amount of 4-aminopyridine in the compressed core is about 16.5 mg.

In one embodiment, the ratio of the amount of the ethylcellulose coat surrounding the compressed core to the amount of 4-aminopyridine in the compressed core is in the range of about 0.5:1 to about 3:1; wherein for calculating said ratio, the amount of the ethylcellulose coat is the weight percentage of the ethylcellulose coat by weight of the compressed core, and the amount of 4-aminopyridine is the weight percentage of 4-aminopyridine by weight of the compressed core. In a preferred embodiment, this ratio of the amount of the ethylcellulose coat to 4-aminopyridine is in the range of about 1:1 to about 2:1. In a specific embodiment, the ratio of the amount of the ethylcellulose coat to 4-aminopyridine is about 1.6:1. In another specific embodiment, the ratio of the amount of the ethylcellulose coat to 4-aminopyridine is about 1.8:1.

In one embodiment, the ratio of the amount of the ethylcellulose coat surrounding the compressed core to the amount of 4-aminopyridine in the compressed core is in the range of about 0.1:1 to about 0.7:1; wherein for calculating said ratio, the amount of the ethylcellulose coat is the weight percentage of the ethylcellulose coat by weight of the compressed core, and the amount of 4-aminopyridine is the weight in milligrams of 4-aminopyridine. In a preferred embodiment, this ratio of the amount of the ethylcellulose coat to 4-aminopyridine is in the range of about 0.2:1 to about 0.5:1. In a specific embodiment, the ratio of the amount of the ethylcellulose coat to 4-aminopyridine is about 0.35:1. In another specific embodiment, the ratio of the amount of the ethylcellulose coat to 4-aminopyridine is about 0.4:1.

In a specific embodiment, the coated compressed core is subjected to a post coating thermal treatment, also referred to as a curing step. In a specific embodiment, the curing step comprises heating the coated compressed core to a temperature above 23° C. for a period of time of at least 15 minutes. In a specific embodiment, the curing step comprises exposing the coated compressed core to a temperature in the range of 40-70° C. for a period of time of at least 15 minutes, 30 minutes, 1 hour, 6 hours, 12 hours, 18 hours, 24 hours, 30 hours, 36 hours, 42 hours or 48 hours. In a specific embodiment, the period of time is at least 1 hour. In a specific embodiment, the period of time is at least 6 hours. In a specific embodiment, the period of time is at least 12 hours. In a specific embodiment, the period of time is at least 18 hours. In a specific embodiment, the period of time is at least 24 hours. In a specific embodiment, the period of time is at least 30 hours. In a specific embodiment, the period of time is at least 36 hours. In a specific embodiment, the period of time is at least 42 hours. In a specific embodiment, the period of time is at least 48 hours. In a specific embodiment, the period of time is at least one of the foregoing, but not more than 48 hours. In a specific embodiment, the coated compressed core is exposed to a temperature in the range of 50-60° C. In a specific embodiment, the curing step comprises exposing the coated compressed core to a temperature in the range of 40-70° C. for a period of time of at least 1 hour. In a specific embodiment, the curing step comprises exposing the coated compressed core to a temperature in the range of 50-60° C. for a period of time of at least 1 hour. In a specific embodiment, the curing step comprises exposing the coated compressed core to a temperature in the range of 50-60° C. for a period of time in the range of 1-48 hours. The curing step of the present invention aims at stabilizing the drug release profile on storage.

In one embodiment, provided herein is a sustained release tablet comprising:
 (a) a compressed core, wherein said compressed core comprises: (i) 4-aminopyridine; (ii) a polyethylene oxide with a molecular weight between about 1,000,000 and 10,000,000, wherein the amount of the polyethylene oxide is in the range of about 12% w/w to about 20% w/w of the compressed core; (iii) a mixture consisting of about 80% polyvinyl acetate, about 19% polyvinyl pyrrolidone, about 0.8% sodium lauryl sulfate, and about 0.2% of silica, wherein the amount of the mixture is in the range of about 20% w/w to about 30% w/w of the compressed core; (iv) dibasic calcium phosphate dihydrate, wherein the amount of dibasic calcium phosphate dihydrate is in the range of about 50% w/w to about 60% w/w of the compressed core; and (v) magnesium stearate, wherein the amount of magnesium stearate is in the range of about 0.7% w/w to about 1.3% w/w of the compressed core; and
 (b) an amount of an ethylcellulose coat surrounding said compressed core;
 wherein the ratio of the amount of the ethylcellulose coat to the amount of 4-aminopyridine in the compressed core is in the range of about 1:1 to about 2:1; wherein for calculating said ratio, the amount of the ethylcellulose coat is the weight percentage of the ethylcellulose coat by weight of the compressed core, and the amount of 4-aminopyridine is the weight percentage of 4-aminopyridine by weight of the compressed core.

In a specific embodiment of the foregoing, the sustained release tablet is the product of a process comprising a curing step after coating the compressed core with ethylcellulose, wherein said curing step comprises exposing the coated compressed core to a temperature in the range of 50-60° C. for a period of time of at least 1 hour.

In one embodiment, provided herein is a sustained release tablet comprising:
 (a) a compressed core, wherein said compressed core comprises: (i) 4-aminopyridine; (ii) a polyethylene oxide with a molecular weight between about 1,000,000 and 10,000,000, wherein the amount of the polyethylene oxide is in the range of about 12% w/w to about 20% w/w of the compressed core; (iii) a mixture consisting of about 80% polyvinyl acetate, about 19% polyvinyl pyrrolidone, about 0.8% sodium lauryl sulfate, and about 0.2% of silica, wherein the amount of the mixture is in the range of about 20% w/w to about 30% w/w of the compressed core; (iv) dibasic calcium phosphate dihydrate, wherein the amount of dibasic calcium phosphate dihydrate is in the range of about 50% w/w to about 60% w/w of the compressed core; and (v) magnesium stearate, wherein the amount of magnesium stearate is in the range of about 0.7% w/w to about 1.3% w/w of the compressed core; and
 (b) an amount of an ethylcellulose coat surrounding said compressed core;
 wherein the ratio of the amount of the ethylcellulose coat to the amount of 4-aminopyridine in the compressed core is in the range of about 0.2:1 to about 0.5:1; wherein for calculating said ratio, the amount of the ethylcellulose coat is the weight percentage of the ethylcellulose coat by weight of the compressed core, and the amount of 4-aminopyridine is the weight in milligrams of 4-aminopyridine.

In a specific embodiment of the foregoing, the sustained release tablet is the product of a process comprising a curing step after coating the compressed core with ethylcellulose, wherein said curing step comprises exposing the coated compressed core to a temperature in the range of 50-60° C. for a period of time of at least 1 hour.

In one embodiment, provided herein is a sustained release tablet comprising:
 (a) a compressed core, said compressed core comprising 4-aminopyridine, a polyethylene oxide with a molecular weight between about 1,000,000 and 10,000,000, and a mixture comprising polyvinyl acetate and polyvinyl pyrrolidone; and
 (b) an amount of an ethylcellulose coat surrounding said compressed core, said amount of the ethylcellulose coat being in the range of about 5% w/w to about 10% w/w of the compressed core.

In a specific embodiment of the foregoing, the sustained release tablet is the product of a process comprising a curing step after coating the compressed core with ethylcellulose, and wherein said curing step comprises heating the coated compressed core to a temperature above 23° C. for a period of time of at least 15 minutes In one embodiment, provided herein is a sustained release tablet comprising:
 (a) a compressed core, wherein said compressed core comprises: (i) 4-aminopyridine; (ii) a polyethylene oxide with a molecular weight between about 1,000,000 and 10,000,000; (iii) a mixture consisting of about 80% polyvinyl acetate, about 19% polyvinyl pyrrolidone, about 0.8% sodium lauryl sulfate, and about 0.2% of silica; (iv) dibasic calcium phosphate dihydrate; and (v) magnesium stearate; and
 (b) an amount of an ethylcellulose coat surrounding said compressed core, said amount of the ethylcellulose coat being in the range of about 5% w/w to about 10% w/w of the compressed core, and wherein the amount of 4-aminopyridine is in the range of about 4% w/w to about 6% w/w of the compressed core.

In a specific embodiment of the foregoing, the sustained release tablet is the product of a process comprising a curing step after coating the compressed core with ethylcellulose, and wherein said curing step comprises exposing the coated compressed core to a temperature in the range of 50-60° C. for a period of time of at least 1 hour In one embodiment, provided herein is a sustained release tablet comprising:
 (a) a compressed core, wherein said compressed core comprises: (i) 4-aminopyridine, wherein the amount of 4-aminopyridine is in the range of about 4% w/w to about 6% w/w of the compressed core; (ii) a polyethylene oxide with a molecular weight between about 1,000,000 and 10,000,000, wherein the amount of the polyethylene oxide is in the range of about 12% w/w to about 20% w/w of the compressed core; (iii) a mixture consisting of about 80% polyvinyl acetate, about 19% polyvinyl pyrrolidone, about 0.8% sodium lauryl sulfate, and about 0.2% of silica, wherein the amount of the mixture is in the range of about 20% w/w to about 30% w/w of the compressed core; (iv) dibasic calcium phosphate dihydrate, wherein the amount of dibasic calcium phosphate dihydrate is in the range of about 50% w/w to about 60% w/w of the compressed core; and (v) magnesium stearate, wherein the amount of magnesium stearate is in the range of about 0.7% w/w to about 1.3% w/w of the compressed core; and (b) an amount of an ethylcellulose coat surrounding said compressed core, said amount of the ethylcellulose coat being in the range of about 5% w/w to about 10% w/w of the compressed core.

In a specific embodiment of the foregoing, the sustained release tablet is the product of a process comprising a curing step after coating the compressed core with ethylcellulose, wherein said curing step comprises exposing the coated compressed core to a temperature in the range of 50-60° C. for a period of time of at least 1 hour.

In a specific embodiment, the sustained release tablet comprises:

(a) a compressed core, wherein said compressed core comprises: (i) 4-aminopyridine, wherein the amount of 4-aminopyridine is in the range of about 4% w/w to about 6% w/w of the compressed core, (ii) a polyethylene oxide with a molecular weight of 7,000,000, wherein the amount of the polyethylene oxide is about 15% w/w of the compressed core, (iii) a mixture consisting of about 80% polyvinyl acetate, about 19% polyvinyl pyrrolidone, about 0.8% sodium lauryl sulfate, and about 0.2% of silica, wherein the amount of the mixture is about 25% w/w of the compressed core, (iv) dibasic calcium phosphate dihydrate in an amount of about 54% w/w of the compressed core, and (v) magnesium stearate in an amount of about 1%; and (b) an amount of an ethylcellulose coat surrounding said compressed core, said amount of the ethylcellulose coat being about 9% w/w of the compressed core.

In a specific aspect of the foregoing embodiment, the amount of 4-aminopyridine in the compressed core is about 5% w/w of the compressed core.

In a specific embodiment of the foregoing, the sustained release tablet is the product of a process comprising a curing step after coating the compressed core with ethylcellulose, and wherein said curing step comprises exposing the coated compressed core to a temperature in the range of 50-60° C. for a period of time of at least 1 hour.

In another specific embodiment, the sustained release tablet comprises:

(a) a compressed core, wherein said compressed core comprises: (i) 4-aminopyridine, wherein the amount of 4-aminopyridine is in the range of about 4% w/w to about 6% w/w of the compressed core, (ii) a polyethylene oxide with a molecular weight of 7,000,000, wherein the amount of the polyethylene oxide is about 15% w/w of the compressed core, (iii) a mixture consisting of about 80% polyvinyl acetate, about 19% polyvinyl pyrrolidone, about 0.8% sodium lauryl sulfate, and about 0.2% of silica, wherein the amount of the mixture is about 25% w/w of the compressed core, (iv) dibasic calcium phosphate dihydrate in an amount of about 54% w/w of the compressed core, and (v) magnesium stearate in an amount of about 1%; and (b) an amount of an ethylcellulose coat surrounding said compressed core, said amount of the ethylcellulose coat being about 5% w/w of the compressed core.

In a specific aspect of the foregoing embodiment, the amount of 4-aminopyridine in the compressed core is about 5% w/w of the compressed core.

In a specific embodiment of the foregoing, the sustained release tablet is the product of a process comprising a curing step after coating the compressed core with ethylcellulose, and wherein said curing step comprises exposing the coated compressed core to a temperature in the range of 50-60° C. for a period of time of at least 1 hour.

In one embodiment, provided herein is a sustained release tablet comprising:

(a) a compressed core, said compressed core comprising 4-aminopyridine, a polyethylene oxide with a molecular weight between about 1,000,000 and 10,000,000, and a mixture comprising polyvinyl acetate and polyvinyl pyrrolidone; and (b) an amount of an ethylcellulose coat surrounding said compressed core, said amount of the ethylcellulose coat being in the range of about 5% w/w to about 7% w/w of the compressed core.

In a specific embodiment of the foregoing, the sustained release tablet is the product of a process comprising a curing step after coating the compressed core with ethylcellulose, and wherein said curing step comprises heating the coated compressed core to a temperature above 23° C. for a period of time of at least 15 minutes.

In one embodiment, provided herein is a sustained release tablet comprising:

(a) a compressed core, wherein said compressed core comprises: (i) 4-aminopyridine; (ii) a polyethylene oxide with a molecular weight between about 1,000,000 and 10,000,000; (iii) a mixture consisting of about 80% polyvinyl acetate, about 19% polyvinyl pyrrolidone, about 0.8% sodium lauryl sulfate, and about 0.2% of silica; (iv) dibasic calcium phosphate dihydrate; and (v) magnesium stearate; and (b) an amount of an ethylcellulose coat surrounding said compressed core, said amount of the ethylcellulose coat being in the range of about 5% w/w to about 7% w/w of the compressed core, and wherein the amount of 4-aminopyridine is in the range of about 3% w/w to about 5% w/w of the compressed core.

In a specific embodiment of the foregoing, the sustained release tablet is the product of a process comprising a curing step after coating the compressed core with ethylcellulose, and wherein said curing step comprises exposing the coated compressed core to a temperature in the range of 50-60° C. for a period of time of at least 1 hour In one embodiment, provided herein is a sustained release tablet comprising:

(a) a compressed core, wherein said compressed core comprises: (i) 4-aminopyridine, wherein the amount of 4-aminopyridine is about 3% w/w to about 5% w/w of the compressed core; (ii) a polyethylene oxide with a molecular weight between about 1,000,000 and 10,000,000, wherein the amount of the polyethylene oxide is in the range of about 12% w/w to about 20% w/w of the compressed core; (iii) a mixture consisting of about 80% polyvinyl acetate, about 19% polyvinyl pyrrolidone, about 0.8% sodium lauryl sulfate, and about 0.2% of silica, wherein the amount of the mixture is in the range of about 20% w/w to about 30% w/w of the compressed core; (iv) dibasic calcium phosphate dihydrate, wherein the amount of dibasic calcium phosphate dihydrate is in the range of about 50% w/w to about 60% w/w of the compressed core; and (v) magnesium stearate, wherein the amount of magnesium stearate is in the range of about 0.7% w/w to about 1.3% w/w of the compressed core; and (b) an amount of an ethylcellulose coat surrounding said compressed core, said amount of the ethylcellulose coat being in the range of about 5% w/w to about 7% w/w of the compressed core.

In a specific embodiment of the foregoing, the sustained release tablet is the product of a process comprising a curing step after coating the compressed core with ethylcellulose, wherein said curing step comprises exposing the coated compressed core to a temperature in the range of 50-60° C. for a period of time of at least 1 hour.

In a specific embodiment, the sustained release tablet comprises:

(a) a compressed core, wherein said compressed core comprises: (i) 4-aminopyridine, wherein the amount of 4-aminopyridine is in the range of about 3% w/w to about 5% w/w of the compressed core, (ii) a polyethylene oxide with a molecular weight of 7,000,000, wherein the amount of the polyethylene oxide is about 15% w/w of the compressed core, (iii) a mixture consisting of about 80% polyvinyl acetate, about 19% polyvinyl pyrrolidone, about 0.8% sodium lauryl sulfate, and about 0.2% of silica, wherein the amount of the mixture is about 25% w/w of the compressed core, (iv) dibasic calcium phosphate dihydrate in an amount of about 55% w/w of the compressed core, and (v) magnesium stearate in an amount of about 1%; and (b) an amount of an ethylcellulose coat surrounding said compressed core, said amount of the ethylcellulose coat being about 6% w/w of the compressed core.

In a specific aspect of the foregoing embodiments, the amount of 4-aminopyridine in the compressed core is about 3.75% w/w of the compressed core.

In a specific embodiment of the foregoing, the sustained release tablet is the product of a process comprising a curing step after coating the compressed core with ethylcellulose, and wherein said curing step comprises exposing the coated compressed core to a temperature in the range of 50-60° C. for a period of time of at least 1 hour.

In one embodiment, the sustained release tablet provided herein is optionally coated further with an aqueous film coat containing a small quantity of 4-aminopyridine, referred to herein as the "4-AP drug overcoat" (or "immediate-release 4-AP drug overcoat"), which results in an initial burst (immediate release) of the 4-aminopyridine. This initial burst is preferably followed by a zero order or near zero order release of the drug from the remaining tablet over an extended period of time. In one embodiment, the 4-AP drug overcoat comprises 4-aminopyridine and one or more coating agents. In one embodiment, the coating agent in the 4-AP drug overcoat comprises hydroxypropylmethylcellulose. In another embodiment, the coating agent in the 4-AP drug overcoat comprises polyvinylalcohol. In a specific embodiment, the coating agent in the 4-AP drug overcoat is from OPADRY® film coating system, commercially available from Colorcon. In a specific embodiment, the coating agent in the 4-AP drug overcoat comprises polyvinyl alcohol, talc, polyethylene glycol, and polysorbate 80. In one embodiment, the 4-AP drug overcoat further comprises a coloring agent. In one embodiment, the amount of 4-aminopyridine in the 4-AP drug overcoat is in the range of about 0.1% w/w to 1.5% w/w of the compressed core. In another embodiment, the amount of 4-aminopyridine in the 4-AP drug overcoat is in the range of about 0.1% w/w to about 1.25% w/w, about 0.1% w/w to about 1% w/w, about 0.1% w/w to about 0.75% w/w, about 0.1% w/w to about 0.50% w/w, about 0.1% w/w to about 0.25% w/w; about 0.25% w/w to about 1.5% w/w, about 0.25% w/w to about 1.25% w/w, about 0.25% w/w to about 1% w/w, about 0.25% w/w to about 0.75% w/w, about 0.25% w/w to about 0.5% w/w, about 0.5% w/w to about 1.5% w/w, about 0.5% w/w to about 1% w/w, about 0.5% w/w to about 0.75% w/w, about 1% w/w to about 1.5% w/w, or about 1% w/w to about 1.25% w/w of the compressed core. In a specific embodiment, the amount of 4-aminopyridine in the 4-AP drug overcoat is about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 1% w/w, about 1.05% w/w, about 1.1% w/w, about 1.15% w/w, about 1.2% w/w, about 1.25% w/w, about 1.3% w/w, about 1.35% w/w, about 1.4% w/w, about 1.45% w/w, or about 1.5% w/w of the compressed core. In one embodiment, the amount of 4-aminopyridine in the 4-AP drug overcoat is in the range of about 0.5 mg to about 6.5 mg. In a specific embodiment, the amount of 4-aminopyridine in the 4-AP drug overcoat is in the range of about 0.5 mg to about 6 mg, about 0.5 mg to about 5 mg, about 0.5 mg to about 5 mg, about 0.5 mg to about 3 mg, about 0.5 mg to about 2 mg, about 0.5 mg to about 1 mg, about 1 mg to about 6.5 mg, about 1 mg to about 5 mg, about 1 mg to about 4 mg, about 1 mg to about 3 mg, about 1 mg to about 2 mg, about 2 mg to about 6.5 mg, about 2 mg to about 5 mg, about 2 mg to about 4 mg, about 2 mg to about 3 mg, about 3 mg to about 6.5 mg, about 3 mg to about 5 mg, about 3 mg to about 4 mg, about 4 mg to about 6.5 mg, or about 4 mg to about 5 mg. In another specific embodiment, the amount of 4-aminopyridine in the 4-AP drug overcoat is about 0.5 mg, 1 mg, 1.5 mg, 2 mg, 2.5 mg, 3 mg, 3.5 mg, 4 mg, 4.5 mg, or 5 mg. In one embodiment, the amount of the coating agent in the 4-AP drug overcoat is in the range of about 3% w/w to about 15% w/w of the compressed core. In another embodiment, the amount of the coating agent in the 4-AP drug overcoat is in the range of about 3% w/w to about 12% w/w, about 3% w/w to about 10% w/w, about 3% w/w to about 7.5% w/w, about 3% w/w to about 5% w/w, about 5% w/w to about 12% w/w, about 5% w/w to about 10% w/w, about 5% w/w to about 7.5% w/w, about 7.5% w/w to about 12% w/w, about 7.5% w/w to about 10% w/w, or about 10% w/w to about 12% w/w of the compressed core. In a specific embodiment, the amount of the coating agent in the 4-AP drug overcoat is 7.1%, 7.2%, 7.3%, 7.4%, 7.5%, 7.6%, 7.7%, 7.8%, 7.9%, 8%, 8.1%, 8.2%, 8.3%, 8.4%, 8.5%, 8.6%, 8.7%, 8.8%, 8.9%, 9%, 9.1%, 9.2%, 9.3%, 9.4%, 9.5%, 9.6%, 9.7%, 9.8%, 9.9%, 10%, 10.1%, 10.2%, 10.3%, 10.4%, 10.5%, 10.6%, 10.7%, 10.8%, 10.9%, or 11%, w/w of the compressed core. In one embodiment, the sustained release tablet provided herein is not coated with a 4-AP drug overcoat. In one embodiment, the sustained release tablet provided herein is not coated with an immediate release drug overcoat (of any drug).

In specific embodiments, the sustained release tablets described herein provide for the release of 4-aminopyridine at a sustained rate such that a therapeutically beneficial blood level of the 4-aminopyridine is maintained over a period of at least about 12 hours, preferably about 24 hours or more. In specific embodiments, the sustained release tablets described herein provide for the release of 4-aminopyridine at a sustained rate such that a therapeutically beneficial blood level of the 4-aminopyridine is maintained over a period of at least about 18 hours. Preferably, the amount of the 4-aminopyridine in the sustained release tablets of the present invention establishes a therapeutically useful plasma concentration through once daily administration of the sustained release tablet. In one embodiment, the sustained release tablet described herein releases an amount of 4-aminopyridine that is therapeutically effective over a period of 24 hours upon administration to a human patient or in physiological medium. In one embodiment, the sustained release tablet described herein releases an amount of 4-aminopyridine that is therapeutically effective over a period of 12 or 18 hours upon administration to a human patient or in physiological medium In one embodiment, the sustained release tablet is suitable for once daily oral administration; i.e., the sustained release tablet provides a therapeutically effective amount of 4-aminopyridine to a human patient upon once daily oral administration.

The sustained release tablets described herein provide sustained release of the active substance 4-aminopyridine when subjected to an in vitro dissolution test. The in vitro dissolution test can be carried out according to standard procedures published by USP NF, <711> Dissolution.

In one embodiment, the dissolution profile of the sustained release tablets described herein is determined by subjecting the sustained release tablets to an in vitro dissolution test employing 0.1 N hydrochloric acid as dissolution medium. In another embodiment, the dissolution profile of the sustained release tablets described herein is determined by subjecting the sustained release tablets to an in vitro dissolution test employing 50 mM Phosphate Buffer, pH 6.8 as dissolution medium.

In some embodiments, provided herein are sustained release tablets comprising 4-aminopyridine, wherein the release of the 4-aminopyridine, upon subjecting the sustained release tablet to an in vitro dissolution test employing 50 mM Phosphate Buffer, pH 6.8 as dissolution medium and the conditions described in Table 2, is as follows: (a) within the first 2 hours after the start of the test at most 30% w/w of the total amount of the 4-aminopyridine contained in the sustained release tablet is released. In a preferred embodiment, the sustained release tablet that is subjected to the dissolution test is a tablet in which 4-aminopyridine is present only in the compressed core (which tablet can be the final oral dosage form of a tablet that does not have an immediate release drug overcoat, or can be the tablet that has not yet been coated with the drug overcoat in an embodiment where the final oral dosage form will have a drug overcoat).

In some embodiments, the release of the 4-aminopyridine, upon subjecting the sustained release tablet to an in vitro dissolution test employing 50 mM Phosphate Buffer, pH 6.8 as dissolution medium and the conditions described in Table 2, is as follows: (a) within the first 2 hours after the start of the test at most 30% w/w of the total amount of the 4-aminopyridine contained in the sustained release tablet is released; and (b) within the first 24 hours after the start of the test at least 80% w/w of the total amount of the 4-aminopyridine contained in the sustained release tablet is released. In a preferred embodiment, the sustained release tablet that is subjected to the dissolution test is a tablet in which 4-aminopyridine is present only in the compressed core (which tablet can be the final oral dosage form of a tablet that does not have an immediate release drug overcoat, or can be the tablet that has not yet been coated with the drug overcoat in an embodiment where the final oral dosage form will have a drug overcoat).

In a specific embodiment, provided herein are sustained release tablets comprising 4-aminopyridine, wherein the release of the 4-aminopyridine, upon subjecting the sustained release tablet to an in vitro dissolution test employing 50 mM Phosphate Buffer, pH 6.8 as dissolution medium and the conditions described in Table 2, is as follows: (a) within the first 2 hours after the start of the test at most 20% w/w of the total amount of the 4-aminopyridine contained in the sustained release tablet is released. In some embodiments, the release of the 4-aminopyridine, upon subjecting the sustained release tablet to an in vitro dissolution test employing 50 mM Phosphate Buffer, pH 6.8 as dissolution medium and the conditions described in Table 2, is as follows: (a) within the first 2 hours after the start of the test at most 20% w/w of the total amount of the 4-aminopyridine contained in the sustained release tablet is released; and (b) within the first 24 hours after the start of the test at least 80% w/w of the total amount of the 4-aminopyridine contained in the sustained release tablet is released. In a preferred embodiment, the sustained release tablet that is subjected to the dissolution test is a tablet in which 4-aminopyridine is present only in the compressed core (which tablet can be the final oral dosage form of a tablet that does not have an immediate release drug overcoat, or can be the tablet that has not yet been coated with the drug overcoat in an embodiment where the final oral dosage form will have a drug overcoat).

In a specific embodiment, the release of the 4-aminopyridine, upon subjecting the sustained release tablet to an in vitro dissolution test employing 50 mM Phosphate Buffer, pH 6.8 as dissolution medium and the conditions described in Table 2, is as follows: (a) within the first 2 hours after the start of the test at most 30% w/w of the total amount of the 4-aminopyridine contained in the sustained release tablet is released; (b) within the first 10 hours after the start of the test at least 50% w/w of the total amount of the 4-aminopyridine contained in the sustained release tablet is released; and (c) within the first 18 hours after the start of the test at least 75% w/w of the total amount of the 4-aminopyridine contained in the sustained release tablet is released. In a preferred embodiment, the sustained release tablet that is subjected to the dissolution test is a tablet in which 4-aminopyridine is present only in the compressed core (which tablet can be the final oral dosage form of a tablet that does not have an immediate release drug overcoat, or can be the tablet that has not yet been coated with the drug overcoat in an embodiment where the final oral dosage form will have a drug overcoat).

In a specific embodiment, the release of the 4-aminopyridine, upon subjecting the sustained release tablet to an in vitro dissolution test employing 50 mM Phosphate Buffer, pH 6.8 as dissolution medium and the conditions described in Table 2, is as follows: (a) within the first 2 hours after the start of the test at most 30% w/w of the total amount of the 4-aminopyridine contained in the sustained release tablet is released; (b) within the first 10 hours after the start of the test at least 40% w/w of the total amount of the 4-aminopyridine contained in the sustained release tablet is released; and (c) within the first 24 hours after the start of the test at least 80% w/w of the total amount of the 4-aminopyridine contained in the sustained release tablet is released. In a preferred embodiment, the sustained release tablet that is subjected to the dissolution test is a tablet in which 4-aminopyridine is present only in the compressed core (which tablet can be the final oral dosage form of a tablet that does not have an immediate release drug overcoat, or can be the tablet that has not yet been coated with the drug overcoat in an embodiment where the final oral dosage form will have a drug overcoat).

In a specific embodiment, the release of the 4-aminopyridine, upon subjecting the sustained release tablet to an in vitro dissolution test employing 50 mM Phosphate Buffer, pH 6.8 as dissolution medium and the conditions described in Table 2, is as follows: (a) within the first 2 hours after the start of the test at most 30% w/w of the total amount of the 4-aminopyridine contained in the sustained release tablet is released; (b) within the first 10 hours after the start of the test at least 40% w/w and at most 85% w/w of the total amount of the 4-aminopyridine contained in the sustained release tablet is released; and (c) within the first 24 hours after the start of the test at least 80% w/w of the total amount of the 4-aminopyridine contained in the sustained release tablet is released. In a preferred embodiment, the sustained release tablet that is subjected to the dissolution test is a tablet in which 4-aminopyridine is present only in the compressed core (which tablet can be the final oral dosage form of a tablet that does not have an immediate release drug overcoat, or can be the tablet that has not yet been coated with the drug overcoat in an embodiment where the final oral dosage form will have a drug overcoat).

In a specific embodiment, the release of the 4-aminopyridine, upon subjecting the sustained release tablet to an in vitro dissolution test employing 50 mM Phosphate Buffer, pH 6.8 as dissolution medium and the conditions described in Table 2, is as follows: (a) within the first 2 hours after the start of the test at most 30% w/w of the total amount of the 4-aminopyridine contained in the sustained release tablet is released; (b) within the first 6 hours after the start of the test at least 10% w/w and at most 65% w/w of the total amount of the 4-aminopyridine contained in the sustained release tablet is released; (c) within the first 10 hours after the start of the test at least 40% w/w and at most 85% w/w of the total amount of the 4-aminopyridine contained in the sustained release tablet is released; and (d) within the first 24 hours after the start of the test at least 80% w/w of the total amount of the 4-aminopyridine contained in the sustained release tablet is released. In a preferred embodiment, the sustained release tablet that is subjected to the dissolution test is a tablet in which 4-aminopyridine is present only in the compressed core (which tablet can be the final oral dosage form of a tablet that does not have an immediate release drug overcoat, or can be the tablet that has not yet been coated with the drug overcoat in an embodiment where the final oral dosage form will have a drug overcoat).

In a specific embodiment, the release of the 4-aminopyridine, upon subjecting the sustained release tablet to an in vitro dissolution test employing 50 mM Phosphate Buffer, pH 6.8 as dissolution medium and the conditions described in Table 2, is as follows: (a) within the first 2 hours after the start of the test at most 30% w/w of the total amount of the 4-aminopyridine contained in the sustained release tablet is released; (b) within the first 6 hours after the start of the test at most 60% w/w and at least 10% w/w of the total amount of the 4-aminopyridine contained in the sustained release tablet is released; (c) within the first 10 hours after the start of the test at most 80% w/w and at least 30% w/w of the total amount of the 4-aminopyridine contained in the sustained release tablet is released; and (d) within the first 24 hours after the start of the test at least 85% w/w of the total amount of the 4-aminopyridine contained in the sustained release tablet is released. In a preferred embodiment, the sustained release tablet that is subjected to the dissolution test is a tablet in which 4-aminopyridine is present only in the compressed core (which tablet can be the final oral dosage form of a tablet that does not have an immediate release drug overcoat, or can be the tablet that has not yet been coated with the drug overcoat in an embodiment where the final oral dosage form will have a drug overcoat).

Figure 1:
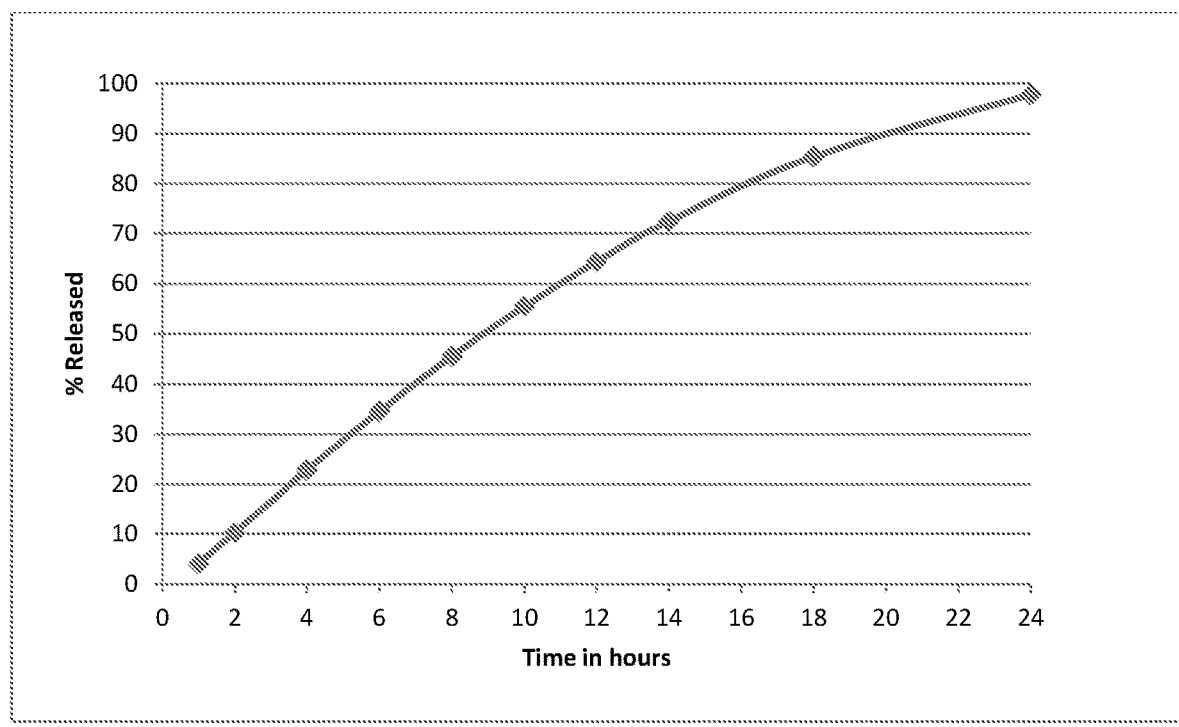
FIG. 1 depicts a dissolution profile of the sustained release tablet in Example 1 employing 50 mM Phosphate Buffer, pH 6.8 as a dissolution medium.

In one embodiment, the sustained release tablet described herein displays a release profile, when tested under the conditions described in Table 2, that when depicted as in FIG. 1, 3, or 4 to graph % release versus time in hours is plus or minus 20% of the data plot depicted in FIG. 1, 3 or 4. In a preferred embodiment, the sustained release tablet that is subjected to the dissolution test is a tablet in which 4-aminopyridine is present only in the compressed core (which tablet can be the final oral dosage form of a tablet that does not have an immediate release drug overcoat, or can be the tablet that has not yet been coated with the drug overcoat in an embodiment where the final oral dosage form will have a drug overcoat).

The in vivo release mechanism of a drug from a sustained release tablet may be altered if the sustained release formulation is administered with alcohol, leading to dose dumping. See, Anand et al., 2011, AAPS J., 13(3):328-335. In a specific embodiment, the total amount of the 4-aminopyridine released, upon subjecting the sustained release tablet to an in vitro dissolution test employing 0.1 N hydrochloric acid containing 40% alcohol (ethanol) as a dissolution medium, within the first 2 hours of the in vitro dissolution test is not greater than the total amount of 4-aminopyridine released within the first 2 hours of an in vitro dissolution test employing 0.1 N hydrochloric acid as dissolution medium.

In a specific embodiment, a sustained release tablet provided herein exhibits substantially no dose dumping in the presence of food (i.e., there are not clinically relevant differences in one or more pharmacokinetic parameters) between fed and fasted states upon administration to patients.

Methods of Making

Provided herein are methods of making a sustained release tablet comprising 4-aminopyridine, which method comprises:

(a) forming a compressed core comprising (i) 4-aminopyridine, (ii) a polyethylene oxide with a molecular weight between about 1,000,000 and 10,000,000, (iii) a mixture comprising polyvinyl acetate and polyvinyl pyrrolidone; (iv) dibasic calcium phosphate dihydrate, and (v) magnesium stearate;

(b) coating the compressed core with an amount of ethylcellulose to form a coated compressed core; and (c) curing the coated compressed core by exposing it to a temperature in the range of 40-70° C. for a period of time of at least 15 minutes, wherein the ratio of the amount of the ethylcellulose coat to the amount of 4-aminopyridine in the compressed core is in the range of about 0.5:1 to about 3:1; wherein for calculating said ratio, the amount of the ethylcellulose coat is the weight percentage of the ethylcellulose coat by weight of the compressed core, and the amount of 4-aminopyridine is the weight percentage of 4-aminopyridine by weight of the compressed core.

In a preferred embodiment of the foregoing embodiment, the ratio of the amount of the ethylcellulose coat to 4-aminopyridine is in the range of about 1:1 to about 2:1.

Also, provided herein are methods of making a sustained release tablet comprising 4-aminopyridine, which method comprises:

(a) forming a compressed core comprising (i) 4-aminopyridine, (ii) a polyethylene oxide with a molecular weight between about 1,000,000 and 10,000,000, (iii) a mixture comprising polyvinyl acetate and polyvinyl pyrrolidone; (iv) dibasic calcium phosphate dihydrate, and (v) magnesium stearate;

(b) coating the compressed core with an amount of ethylcellulose to form a coated compressed core; and (c) curing the coated compressed core by exposing it to a temperature in the range of 40-70° C. for a period of time of at least 15 minutes,
wherein the ratio of the amount of the ethylcellulose coat to the amount of 4-aminopyridine in the compressed core is in the range of about 0.1:1 to about 0.7:1; wherein for calculating said ratio, the amount of the ethylcellulose coat is the weight percentage of the ethylcellulose coat by weight of the compressed core, and the amount of 4-aminopyridine is the weight in milligrams of 4-aminopyridine.

In a preferred embodiment of the foregoing embodiment, the ratio of the amount of the ethylcellulose coat to 4-aminopyridine is in the range of about 0.2:1 to about 0.5:1.

Also, provided herein are methods of making a sustained release tablet comprising 4-aminopyridine, which method comprises:
(a) forming a compressed core comprising (i) 4-aminopyridine, (ii) a polyethylene oxide with a molecular weight between about 1,000,000 and 10,000,000, (iii) a mixture comprising polyvinyl acetate and polyvinyl pyrrolidone; (iv) dibasic calcium phosphate dihydrate, and (v) magnesium stearate;
(b) coating the compressed core with an amount of ethylcellulose to form a coated compressed core, said amount of the ethylcellulose coat being in the range of about 8% w/w to about 10% w/w of the sustained release tablet; and
(c) curing the coated compressed core by heating the coated compressed core to a temperature above 23° C. for a period of time of at least 15 minutes.

Also, provided herein is a method of making a sustained release tablet comprising 4-aminopyridine, which method comprises:
(a) forming a compressed core comprising (i) 4-aminopyridine, (ii) a polyethylene oxide with a molecular weight between about 1,000,000 and 10,000,000, (iii) a mixture comprising polyvinyl acetate and polyvinyl pyrrolidone; (iv) dibasic calcium phosphate dihydrate, and (v) magnesium stearate;
(b) coating the compressed core with an amount of ethylcellulose to form a coated compressed core, said amount of the ethylcellulose coat being in the range of about 5% w/w to about 10% w/w of the compressed core; and
(c) curing the coated compressed core by exposing it to a temperature in the range of 40-70° C. for a period of time of at least 15 minutes.

In a specific embodiment of the foregoing method of making, the amount of the ethylcellulose coat is about 9% w/w of the compressed core and the amount of 4-aminopyridine is in the range of about 4% w/w to about 6% w/w of the compressed core. In another specific embodiment of the foregoing method of making, the amount of the ethylcellulose coat is about 5% w/w of the compressed core and the amount of 4-aminopyridine is in the range of about 4% w/w to about 6% w/w of the compressed core.

Also, provided herein is a method of making a sustained release tablet comprising 4-aminopyridine, which method comprises:
(a) forming a compressed core comprising (i) 4-aminopyridine, (ii) a polyethylene oxide with a molecular weight between about 1,000,000 and 10,000,000, (iii) a mixture comprising polyvinyl acetate and polyvinyl pyrrolidone; (iv) dibasic calcium phosphate dihydrate, and (v) magnesium stearate;
(b) coating the compressed core with an amount of ethylcellulose to form a coated compressed core, said amount of the ethylcellulose coat being in the range of about 5% w/w to about 7% w/w of the compressed core; and
(c) curing the coated compressed core by exposing it to a temperature in the range of 40-70° C. for a period of time of at least 15 minutes.

In a specific embodiment of the foregoing methods of making, the amount of the ethylcellulose coat is about 6% w/w of the compressed core and the amount of 4-aminopyridine is in the range of about 3% w/w to about 5% w/w of the compressed core.

In a specific embodiment, the curing step comprises exposing the coated compressed core to a temperature in the range of 40-70° C. for a period of time of at least 15 minutes, 30 minutes or 1 hour. In a specific embodiment, the curing step comprises exposing the coated compressed core to a temperature in the range of 40-70° C. for a period of time of at least 1 hour.

Also provided herein is a method of making a sustained release tablet comprising 4-aminopyridine, which method comprises:
(a) forming a compressed core comprising (i) 4-aminopyridine, wherein the amount of 4-aminopyridine is in the range of about 4% w/w to about 6% w/w of the compressed core, (ii) a polyethylene oxide with a molecular weight of 7,000,000, wherein the amount of the polyethylene oxide is about 15% w/w of the compressed core, (iii) a mixture consisting of about 80% polyvinyl acetate, about 19% polyvinyl pyrrolidone, about 0.8% sodium lauryl sulfate, and about 0.2% of silica, wherein the amount of the mixture is about 25% w/w of the compressed core; (iv) dibasic calcium phosphate dihydrate, wherein the amount of dibasic calcium phosphate dihydrate is about 54% w/w of the compressed core; and (v) magnesium stearate, wherein the amount of magnesium stearate is about 1% w/w of the compressed core;
(b) coating the compressed core with an amount of ethylcellulose to form a coated compressed core, said amount of the ethylcellulose coat being about 9% w/w of the compressed core; and (c) curing the coated compressed core by exposing it to a temperature in the range of 50-60° C. for a period of time of at least 1 hour.

In a specific embodiment of the foregoing embodiment, the amount of 4-aminopyridine in the compressed core is about 22 mg.

Also provided herein is a method of making a sustained release tablet comprising 4-aminopyridine, which method comprises:
(a) forming a compressed core comprising (i) 4-aminopyridine, wherein the amount of 4-aminopyridine is in the range of about 4% w/w to about 6% w/w of the compressed core, (ii) a polyethylene oxide with a molecular weight of 7,000,000, wherein the amount of the polyethylene oxide is about 15% w/w of the compressed core, (iii) a mixture consisting of about 80% polyvinyl acetate, about 19% polyvinyl pyrrolidone, about 0.8% sodium lauryl sulfate, and about 0.2% of silica, wherein the amount of the mixture is about 25% w/w of the compressed core; (iv) dibasic calcium phosphate dihydrate, wherein the amount of dibasic calcium phosphate dihydrate is about 54% w/w of the compressed core; and (v) magnesium stearate, wherein the amount of magnesium stearate is about 1% w/w of the compressed core;
(b) coating the compressed core with an amount of ethylcellulose to form a coated compressed core, said amount of the ethylcellulose coat being about 5% w/w of the compressed core; and
(c) curing the coated compressed core by exposing it to a temperature in the range of 50-60° C. for a period of time of at least 1 hour.

In a specific embodiment of the foregoing embodiment, the amount of 4-aminopyridine in the compressed core is about 22 mg.

Also provided herein is a method of making a sustained release tablet comprising 4-aminopyridine, which method comprises:
(a) forming a compressed core comprising (i) 4-aminopyridine, wherein the amount of 4-aminopyridine is in the range of about 3% w/w to about 5% w/w of the compressed core, (ii) a polyethylene oxide with a molecular weight of 7,000,000, wherein the amount of the polyethylene oxide is about 15% w/w of the compressed core, (iii) a mixture consisting of about 80% polyvinyl acetate, about 19% polyvinyl pyrrolidone, about 0.8% sodium lauryl sulfate, and about 0.2% of silica, wherein the amount of the mixture is about 25% w/w of the compressed core; (iv) dibasic calcium phosphate dihydrate, wherein the amount of dibasic calcium phosphate dihydrate is about 55% w/w of the compressed core; and (v) magnesium stearate, wherein the amount of magnesium stearate is about 1% w/w of the compressed core;
(b) coating the compressed core with an amount of ethylcellulose to form a coated compressed core, said amount of the ethylcellulose coat being about 6% w/w of the compressed core; and
(c) curing the coated compressed core by exposing it to a temperature in the range of 50-60° C. for a period of time of at least 1 hour.

In a specific embodiment of the foregoing embodiment, the amount of 4-aminopyridine in the compressed core is about 16.5 mg.

In specific embodiments, the methods of making a sustained release tablet comprise, or consist essentially, or consist of, the steps as described herein.

The core is typically formed by first blending the active drug substance (4-aminopyridine), the polymeric components of the formulation, and additional excipients (e.g., filler or binder) for a brief period of time (e.g., 5-20 minutes). This is followed by addition of a suitable lubricant and further blending the mixture to a uniform new blend. The resulting blend is then compressed to intermediate tablets by methods known in the art.

In a specific embodiment, the method of forming the compressed core comprises:
(a) blending the 4-aminopyridine, polyethylene oxide, the mixture comprising polyvinyl acetate and polyvinyl pyrrolidone, and dibasic calcium phosphate dihydrate to form a blended mixture; (b) adding magnesium stearate to the blended mixture to form a new blend; and
(c) compressing the new blend to form a compressed core. In a specific embodiment, the blended mixture and new blend are formed by dry blending.

In a specific embodiment, the polyethylene oxide has a molecular weight between 4,000,000 and 8,000,000. In another specific embodiment, the polyethylene oxide has a molecular weight of 7,000,000. In another specific embodiment, the polyethylene oxide is POLYOX WSR-303, commercially available from Dow Chemical Co. In a specific embodiment, the amount of the polyethylene oxide in the compressed core is in the range of about 10% w/w to about 20% w/w of the compressed core.

In a specific embodiment, the mixture comprising polyvinyl acetate and polyvinyl pyrrolidone consists of about 80% polyvinyl acetate, about 19% polyvinyl pyrrolidone, about 0.8% sodium lauryl sulfate, and about 0.2% of silica. In one embodiment, the mixture comprising polyvinyl acetate and polyvinyl pyrrolidone is KOLLIDON® SR polyvinyl acetate/polyvinyl pyrrolidone (BASF); KOLLIDON® SR is a blend of 80% polyvinyl acetate and 19% povidone (also called polyvinyl pyrrolidone) along with small quantities of sodium lauryl sulfate and silica used as stabilizers (see Signet Chemical Corporation's website page for KOLLIDON® SR). In a specific embodiment, the amount of the mixture comprising polyvinyl acetate and polyvinyl pyrrolidone in the compressed core is in the range of about 20% w/w to about 30% w/w of the compressed core.

In a specific embodiment, the amount of dibasic calcium phosphate dihydrate in the compressed core is in the range of about 47% w/w to about 53% w/w of the sustained release tablet. In another specific embodiment, the amount of dibasic calcium phosphate dihydrate in the compressed core is in the range of about 50% w/w to about 60% w/w of the compressed core.

In a specific embodiment, the amount of magnesium stearate in the compressed core is in the range of about 0.7% w/w to about 1.3% w/w of the sustained release tablet. In another specific embodiment, the amount of magnesium stearate in the compressed core is in the range of about 0.7% w/w to about 1.3% w/w of the compressed core.

The coating of the compressed core (i.e., intermediate tablets) is performed by using methods well known in the art, as described in U.S. Pat. No. 8,858,993. In a specific embodiment, the coating process described herein includes film coating. Tablet coating equipment may include spray guns, coating pans, polishing pans, solution tanks, blenders and mixers, homogenizers, mills, peristaltic pumps, fans, steam jackets, exhaust and heating pipes, scales and filters. In a specific embodiment, the coating method involves spray coating.

As described in U.S. Pat. No. 8,858,993, tablet coating typically takes place in a controlled atmosphere inside a perforated rotating drum. Angled baffles fitted into the drum and air flow inside the drum can provide means of mixing the tablet bed. As a result, the tablets are lifted and turned from the sides into the center of the drum, exposing each tablet surface to an even amount of deposited/sprayed coating. The liquid spray coating is then dried onto the tablets by heated air drawn through the tablet bed from an inlet fan. The air flow is typically regulated for temperature and volume to provide controlled drying and extracting rates, and at the same time, maintaining the drum pressure slightly negative relative to the room in order to provide a completely isolated process atmosphere for the operator.

In a specific embodiment, the coated compressed core is subjected to a post coating thermal treatment, also referred to as a curing step. In a specific embodiment, the curing step comprises heating the coated compressed core to a temperature above 23° C. for a period of time of at least 15 minutes. In a specific embodiment, the curing step comprises exposing the coated compressed core to a temperature in the range of 40-70° C. for a period of time of at least 15 minutes, 30 minutes, 1 hour, 6 hours, 12 hours, 18 hours, 24 hours, 30 hours, 36 hours, 42 hours or 48 hours. In a specific embodiment, the period of time is at least 1 hour. In a specific embodiment, the period of time is at least 6 hours. In a specific embodiment, the period of time is at least 12 hours. In a specific embodiment, the period of time is at least 18 hours. In a specific embodiment, the period of time is at least 24 hours. In a specific embodiment, the period of time is at least 30 hours. In a specific embodiment, the period of time is at least 36 hours. In a specific embodiment, the period of time is at least 42 hours. In a specific embodiment, the period of time is at least 48 hours. In a specific embodiment, the coated compressed core is exposed to a temperature in the range of 50-60° C. In a specific embodiment, the curing step comprises exposing the coated compressed core to a temperature in the range of 40-70° C. for a period of time of at least 1 hour. In a specific embodiment, the curing step comprises exposing the coated compressed core to a temperature in the range of 50-60° C. for a period of time of at least 1 hour. In a specific embodiment, the curing step comprises exposing the coated compressed core to a temperature in the range of 50-60° C. for a period of time in the range of 1-48 hours. The curing step of the present invention aims at stabilizing the drug release profile on storage.

In one embodiment, after the curing step the sustained release tablet is optionally coated further with an aqueous film coat containing a small quantity of 4-aminopyridine, referred to herein as the "4-AP drug overcoat" (or "immediate release 4-AP drug overcoat"), which results in an initial burst (immediate release) of the 4-aminopyridine. This initial burst is preferably followed by a zero order or near zero order release of the drug from the remaining tablet over an extended period of time. In one embodiment, the 4-AP drug overcoat comprises 4-aminopyridine and one or more coating agents. In one embodiment, the coating agent in the 4-AP drug overcoat comprises hydroxypropylmethylcellulose. In another embodiment, the coating agent in the 4-AP drug overcoat comprises polyvinylalcohol. In a specific embodiment, the coating agent in the 4-AP drug overcoat is from OPADRY® film coating system, commercially available from Colorcon. In a specific embodiment, the coating agent in the 4-AP drug overcoat comprises polyvinyl alcohol, talc, polyethylene glycol, and polysorbate 80. In one embodiment, the 4-AP drug overcoat further comprises a coloring agent. A solution of the 4-AP drug overcoat is typically prepared by dissolving a coating agent in a suitable solvent (e.g., water), followed by adding 4-aminopyridine and stirring to obtain a clear solution. The solution of the 4-AP drug overcoat can be applied to the dried coated compressed cores by methods well known in the art to achieve the desired coat weight gain. In one embodiment, the solution is applied by spray coating. After the 4-AP drug overcoat is applied, the resulting tablets can be dried, e.g., for up to 1 h at a temperature of about 50-60° C.

In a specific embodiment the sustained release tablet of the present invention, aside from any immediate release of 4-aminopyridine due to the presence of a 4-AP drug overcoat, provides a zero-order or near-zero-order release of the 4-aminopyridine. In a preferred embodiment, the release is zero-order.

In specific embodiments, the sustained release tablets discussed herein provide for the release of 4-aminopyridine at a sustained rate such that a therapeutically beneficial blood level of the 4-aminopyridine is maintained over a period of at least about 12 hours, preferably about 24 hours or more. In another specific embodiment, the sustained release tablets discussed herein provide for the release of 4-aminopyridine at a sustained rate such that a therapeutically beneficial blood level of the 4-aminopyridine is maintained over a period of at least about 18 hours. Preferably, the amount of the 4-aminopyridine in the sustained release tablets of the present invention establish a therapeutically useful plasma concentration through once daily administration of the sustained release tablet. In one embodiment, the sustained release tablet described herein comprises an amount of 4-aminopyridine that is therapeutically effective over a period of 24 hours. In one embodiment, the sustained release tablet is suitable for once daily oral administration; i.e., the sustained release tablet provides a therapeutically effective of 4-aminopyridine to a human patient upon once daily oral administration.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, or 3 standard deviations. In certain embodiments, the term "about" or "approximately" means within 10%, 9%, 8%, 7%, 6%, 5%, 4%, 3%, 2%, 1%, 0.5%, 0.4%, 0.3%, 0.25%, 0.2%, 0.1% or 0.05% of a given value or range.

5.2 Methods of Treatment

Provided herein are methods of treating a neurological disorder in a patient in need thereof comprising orally administering to the patient a sustained release 4-aminopyridine tablet as disclosed herein.

In one embodiment, provided herein are methods of treating a neurological disorder in a patient in need thereof comprising orally administering to the patient once daily a sustained release tablet comprising:

(a) a compressed core, wherein said compressed core comprises (i) 4-aminopyridine, wherein the amount of 4-aminopyridine is in the range of about 4% w/w to about 6% w/w of the compressed core; (ii) a polyethylene oxide with a molecular weight of 7,000,000, wherein the amount of the polyethylene oxide is about 15% w/w of the compressed core; (iii) a mixture consisting of about 80% polyvinyl acetate, about 19% polyvinyl pyrrolidone, about 0.8% sodium lauryl sulfate, and about 0.2% of silica, wherein the amount of the mixture is about 25% w/w of the compressed core; (iv) dibasic calcium phosphate dihydrate, wherein the amount of dibasic calcium phosphate dihydrate is about 54% w/w of the compressed core; and (v) magnesium stearate, wherein the amount of magnesium stearate is about 1% w/w of the compressed core;

and (b) an amount of an ethylcellulose coat surrounding said compressed core, said amount of the ethylcellulose coat being about 9% w/w of the compressed core.

In one embodiment of the foregoing embodiment, the amount of 4-aminopyridine in the compressed core is about 17.5 mg, about 18 mg, about 18.5 mg, about 19 mg, about 19.5 mg, about 20 mg, about 20.5 mg, about 21 mg, about 21.5 mg, about 22 mg, about 22.5 mg, about 23 mg, about 23.5 mg, about 24 mg, about 24.5 mg, about 25 mg, about 25.5 mg, about 26 mg, or about 26.5 mg. In a specific embodiment of the foregoing embodiment, the amount of 4-aminopyridine in the compressed core is about 22 mg.

In a specific embodiment of the foregoing, the sustained release tablet is the product of a process comprising a curing step after coating the compressed core with ethylcellulose, wherein said curing step comprises exposing the coated compressed core to a temperature in the range of 50-60° C. for a period of time of at least 1 hour.

In one embodiment, provided herein are methods of treating a neurological disorder in a patient in need thereof comprising orally administering to the patient once daily a sustained release tablet comprising:

(a) a compressed core, wherein said compressed core comprises (i) 4-aminopyridine, wherein the amount of 4-aminopyridine is in the range of about 4% w/w to about 6% w/w of the compressed core; (ii) a polyethylene oxide with a molecular weight of 7,000,000, wherein the amount of the polyethylene oxide is about 15% w/w of the compressed core; (iii) a mixture consisting of about 80% polyvinyl acetate, about 19% polyvinyl pyrrolidone, about 0.8% sodium lauryl sulfate, and about 0.2% of silica, wherein the amount of the mixture is about 25% w/w of the compressed core; (iv) dibasic calcium phosphate dihydrate, wherein the amount of dibasic calcium phosphate dihydrate is about 54% w/w of the compressed core; and (v) magnesium stearate, wherein the amount of magnesium stearate is about 1% w/w of the compressed core; and (b) an amount of an ethylcellulose coat surrounding said compressed core, said amount of the ethylcellulose coat being about 5% w/w of the compressed core.

In one embodiment of the foregoing embodiment, the amount of 4-aminopyridine in the compressed core is about 17.5 mg, about 18 mg, about 18.5 mg, about 19 mg, about 19.5 mg, about 20 mg, about 20.5 mg, about 21 mg, about 21.5 mg, about 22 mg, about 22.5 mg, about 23 mg, about 23.5 mg, about 24 mg, about 24.5 mg, about 25 mg, about 25.5 mg, about 26 mg, or about 26.5 mg. In a specific embodiment of the foregoing embodiment, the amount of 4-aminopyridine in the compressed core is about 22 mg.

In a specific embodiment of the foregoing, the sustained release tablet is the product of a process comprising a curing step after coating the compressed core with ethylcellulose, wherein said curing step comprises exposing the coated compressed core to a temperature in the range of 50-60° C. for a period of time of at least 1 hour.

In one embodiment, provided herein are methods of treating a neurological disorder in a patient in need thereof comprising orally administering to the patient once daily a sustained release tablet comprising:

(a) a compressed core, wherein said compressed core comprises (i) 4-aminopyridine, wherein the amount of 4-aminopyridine is in the range of about 3% w/w to about 5% w/w of the compressed core; (ii) a polyethylene oxide with a molecular weight of 7,000,000, wherein the amount of the polyethylene oxide is about 15% w/w of the compressed core; (iii) a mixture consisting of about 80% polyvinyl acetate, about 19% polyvinyl pyrrolidone, about 0.8% sodium lauryl sulfate, and about 0.2% of silica, wherein the amount of the mixture is about 25% w/w of the compressed core; (iv) dibasic calcium phosphate dihydrate, wherein the amount of dibasic calcium phosphate dihydrate is about 55% w/w of the compressed core; and (v) magnesium stearate, wherein the amount of magnesium stearate is about 1% w/w of the compressed core; and (b) an amount of an ethylcellulose coat surrounding said compressed core, said amount of the ethylcellulose coat being about 6% w/w of the compressed core.

In one embodiment of the foregoing embodiment, the amount of 4-aminopyridine in the compressed core is about 13 mg, about 13.5 mg, about 14 mg, about 14.5 mg, about 15 mg, about 15.5 mg, about 16 mg, about 16.5 mg, about 17 mg, about 17.5 mg, about 18 mg, about 18.5 mg, about 19 mg, about 19.5 mg, about 20 mg, about 20.5 mg, about 21 mg, about 21.5 mg or about 22 mg. In a specific embodiment of the foregoing embodiment, the amount of 4-aminopyridine in the compressed core is about 16.5 mg.

In a specific embodiment of the foregoing, the sustained release tablet is the product of a process comprising a curing step after coating the compressed core with ethylcellulose, wherein said curing step comprises exposing the coated compressed core to a temperature in the range of 50-60° C. for a period of time of at least 1 hour.

"Patient" is defined herein to include animals, such as mammals, including, but not limited to, primates (e.g., humans), cows, sheep, goats, horses, dogs, cats, rabbits, rats, mice, monkeys, chickens, turkeys, quails, or guinea pigs and the like. In one embodiment, the patient is a mammal. In a preferred embodiment, the patient is a human patient.

In a specific embodiment, the human patient is an adult (e.g., greater than 16 years of age). In another specific embodiment, the patient is a pediatric patient (e.g., age 2-16). In one embodiment, the age of the pediatric patient is at least 6 years. In another specific embodiment, the human patient is an adolescent (e.g., age 12-16). In another specific embodiment, the patient is a child (e.g. age 2-12). In one embodiment, the age of the child is at least 6 years.

In one embodiment, the administering to the patient is performed once daily. In another embodiment, the administering to the patient is performed twice daily.

The neurological disorder is a neurological disorder amenable to treatment by 4-aminopyridine. In certain embodiments, the neurological disorder is a neurological disease including, but not limited to, multiple sclerosis and stroke. In a specific embodiment, the neurological disorder is multiple sclerosis. In another specific embodiment, the neurological disorder is stroke. In some embodiments, the neurological disorder is an impairment associated with a neurological disease. In one embodiment, the neurological disorder is a walking impairment associated with multiple sclerosis. In a specific embodiment, the method of treatment is to improve walking or to increase walking speed in a multiple sclerosis patient. In a specific embodiment, the method of treatment is to improve walking or to increase walking speed in a stroke patient. In one embodiment, the neurological disorder is a neurocognitive or a neuropsychiatric impairment associated with multiple sclerosis. In one embodiment, the neurological disorder is a sensorimotor impairment associated with stroke. In one embodiment, the neurological disorder is a walking impairment associated with stroke.

In a specific embodiment, the invention provides a method of improving walking comprising administering once daily to a patient (e.g., a multiple sclerosis patient) a sustained release tablet provided herein.

In one embodiment, the sustained release 4-aminopyridine tablet as disclosed herein is orally administered to a patient with renal impairment, for example, a patient who is mildly or moderately renally impaired. In one embodiment, the renal impairment is mild renal impairment. In one embodiment, the renal impairment is moderate renal impairment. In one embodiment, the renal impairment is severe renal impairment. In one embodiment, the renal impairment is moderate or severe renal impairment. In another embodiment, the sustained release 4-aminopyridine tablet is orally administered to a patient who is not severely renal impaired. In one embodiment, the patient is classified as having mild renal impairment when the patient has a creatinine clearance value in the range of 51-80 mL/min. In another embodiment, the patient is classified as having mild renal impairment when the patient has a creatinine clearance value in the range of 60-89 mL/min. In yet another embodiment, the patient is classified as having mild renal impairment when the patient has an estimated glomerular filtration rate in the range of 60-89 mL/min/1.73 m$^2$. In one embodiment, the patient is classified as having moderate renal impairment when the patient has a creatinine clearance value in the range of 30-59 mL/min. In yet another embodiment, the patient is classified as having moderate renal impairment when the patient has an estimated glomerular filtration rate in the range of 30-59 mL/min/1.73 m$^2$. In one embodiment, the patient is classified as having severe renal impairment when the patient has a creatinine clearance value in the range of 15-29 mL/min. In yet another embodiment, the patient is classified as having severe renal impairment when the patient has an estimated glomerular filtration rate in the range of 15-29 mL/min/1.73 m².

In a specific embodiment, the sustained release tablet as disclosed herein is orally administered once daily to an adult or adolescent patient, wherein the compressed core of the sustained release tablet comprises 4-aminopyridine in an amount in the range of about 5 mg to about 40 mg. In a specific embodiment of the foregoing, the amount of 4-aminopyridine in the compressed core is in the range of about 5 mg to about 35 mg, about 5 mg to about 30 mg, about 5 mg to about 25 mg, about 5 mg to about 20 mg, about 5 mg to about 15 mg, about 5 mg to about 10 mg, about 10 mg to about 40 mg, about 10 mg to about 35 mg, about 10 mg to about 30 mg, about 10 mg to about 25 mg, about 10 mg to about 20 mg, about 10 mg to about 15 mg, about 15 mg to about 40 mg, about 15 mg to about 35 mg, about 15 mg to about 30 mg, about 15 mg to about 25 mg, about 15 mg to about 20 mg, about 20 mg to about 40 mg, about 20 mg to about 35 mg, about 20 mg to about 30 mg, about 20 mg to about 25 mg, about 25 mg to about 40 mg, about 25 mg to about 35 mg, about 25 mg to about 30 mg, about 30 mg to about 40 mg, about 30 mg to about 35 mg, or about 35 mg to about 40 mg. In another specific embodiment of the foregoing, the amount of 4-aminopyridine in the compressed core is about 16 mg, about 16.2 mg, about 16.4 mg, about 16.6 mg, about 16.8 mg, about 17 mg, about 17.2 mg, about 17.4 mg, about 17.6 mg, about 17.8 mg, about 18 mg, about 18.2 mg, about 18.4 mg, about 18.6 mg, about 18.8 mg, about 19 mg, about 19.2 mg, about 19.4 mg, about 19.6 mg, about 19.8 mg, about 20 mg, about 20.2 mg, about 20.4 mg, about 20.6 mg, about 20.8 mg, about 21 mg, about 21.2 mg, about 21.4 mg, about 21.6 mg, about 21.8 mg, about 22 mg, about 22.2 mg, about 22.4 mg, about 22.6 mg, about 22.8 mg, about 23 mg, about 23.2 mg, about 23.4 mg, about 23.6 mg, about 23.8 mg, about 24 mg, about 24.2 mg, about 24.4 mg, about 24.6 mg, about 24.8 mg, or about 25 mg. In another embodiment of the foregoing, the amount of 4-aminopyridine in the compressed core is in the range of about 12 mg to about 40 mg. In another embodiment of the foregoing, the amount of 4-aminopyridine in the compressed core is in the range of about 12 mg to about 25 mg. In another embodiment of the foregoing, the amount of 4-aminopyridine in the compressed core is in the range of about 12 mg to about 15 mg. In another embodiment of the foregoing, the amount of 4-aminopyridine in the compressed core is in the range of about 5 mg to about 12 mg. In a specific embodiment of the foregoing, the amount of 4-aminopyridine in the compressed core is about 22 mg. In another specific embodiment of the foregoing, the amount of 4-aminopyridine in the compressed core is about 16.5 mg. In another specific embodiment of the foregoing, the amount of 4-aminopyridine in the compressed core is about 11 mg. In a specific embodiment, the sustained release tablet as disclosed herein is orally administered once daily to an adult patient, wherein the compressed core of the sustained release tablet comprises 4-aminopyridine in an amount in the range of about 16 mg to about 22 mg. In another specific embodiment, the sustained release tablet as disclosed herein is orally administered once daily to an adolescent patient, wherein the compressed core of the sustained release tablet comprises 4-aminopyridine in an amount in the range of about 12 mg to about 22 mg. In another specific embodiment, the sustained release tablet as disclosed herein is orally administered once daily to a child patient of age 6-12, wherein the compressed core of the sustained release tablet comprises 4-aminopyridine in an amount in the range of about 4 mg to about 13 mg.

In a specific embodiment, the sustained release tablet as disclosed herein is orally administered once daily to a pediatric patient, wherein the compressed core of the sustained release tablet comprises 4-aminopyridine in an amount in the range of about 4 mg to about 13 mg. In a specific embodiment of the foregoing, the amount of 4-aminopyridine in the compressed core is in the range of about 4 mg to about 11 mg, about 4 mg to about 9 mg, about 4 mg to about 7 mg, about 4 mg to about 5 mg, about 5 mg to about 13 mg, about 5 mg to about 11 mg, about 5 mg to about 9 mg, about 5 mg to about 7 mg, about 7 mg, to about 13 mg, about 7 mg to about 11 mg, about 7 mg to about 9 mg, about 9 mg to about 13 mg, about 9 mg to about 11 mg, or about 11 mg to about 13 mg. In another specific embodiment of the foregoing, the amount of 4-aminopyridine in the compressed core is about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, or about 12 mg. In another specific embodiment of the foregoing, the amount of 4-aminopyridine in the compressed core is about 11 mg. In another specific embodiment of the foregoing, the amount of 4-aminopyridine in the compressed core is about 8 mg. In one embodiment, the pediatric dose is half of the adult dose. For example, if the amount of 4-aminopyridine in the compressed core orally administered once daily to an adult patient is about 22 mg, the amount of 4-aminopyridine in the compressed core orally administered to a pediatric patient is about 11 mg.

In one embodiment, the sustained release tablet as disclosed herein is orally administered once daily to a patient with renal impairment, wherein the compressed core of the sustained release tablet comprises 4-aminopyridine in an amount in the range of about 4 mg to about 20 mg. In a specific embodiment of the foregoing, the amount of 4-aminopyridine in the compressed core is about 6 mg to about 20 mg, about 6 mg to about 16 mg, about 6 mg to about 12 mg, about 6 mg to about 18 mg, about 8 mg to about 20 mg, about 8 mg to about 16 mg, about 8 mg to about 12 mg, about 10 mg to about 20 mg, about 10 mg to about 16 mg, about 10 mg to about 12 mg, about 12 mg to about 20 mg, about 12 mg to about 16 mg, about 14 mg to about 20 mg, about 14 mg to about 16 mg, or about 16 mg to about 20 mg. In a specific embodiment of the foregoing, the amount of 4-aminopyridine in the compressed core is about 7 mg to about 9 mg. In another specific embodiment of the foregoing, the amount of 4-aminopyridine in the compressed core is about 11 mg to about 13 mg. In another specific embodiment of the foregoing, the amount of 4-aminopyridine in the compressed core is about 12 mg to about 15 mg. In another specific embodiment of the foregoing, the amount of 4-aminopyridine in the compressed core is about 15 mg to about 17 mg. In another specific embodiment of the foregoing, the amount of 4-aminopyridine in the compressed core is about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5 mg, about 15 mg, about 15.5 mg, about 16 mg, about 16.5 mg or about 17 mg. In a specific embodiment, the sustained release tablet of any of the foregoing embodiments is orally administered once daily to a patient with mild or moderate renal impairment.

In one embodiment, the sustained release 4-aminopyridine tablet as disclosed herein is orally administered once daily to a patient with no renal impairment. In one embodiment, the patient is classified as having no renal impairment when the patient has an estimated glomerular filtration rate of ≥90 mL/min/1.73 m². In one embodiment, the patient is classified as having no renal impairment when the patient has a creatinine clearance value of ≥90 mL/min.

Preferably, a sustained release 4-aminopyridine tablet as disclosed herein, upon oral administration to human subjects does not result in substantial dose dumping in the presence of food. In one embodiment, the sustained release 4-aminopyridine tablet, upon oral administration to human subjects does not result in clinically relevant differences in pharmacokinetic parameters such as AUC or $C_{max}$ between the fed or fasted conditions when administered to human subjects in fed and fasted conditions. In one embodiment, a human subject having consumed a high-fat high-calorie meal before oral administration (as described in Guidance for Industry, Food-Effect Bioavailability and Fed Bioequivalence Studies, U.S. Department of Health and Human Services, Food and Drug Administration, December 2002) is considered to be in a fed state. In one embodiment, a human subject observing an overnight fast of at least 10 h is considered to be in a fasted state.

In a specific embodiment, a sustained release 4-aminopyridine tablet as disclosed herein, upon oral administration to human subjects in a fasted state, provides one or more of the following pharmacokinetic parameters: (a) a mean plasma 4-aminopyridine $C_{max}$ in the range of about 14.74 ng/mL to about 20.66 ng/mL; (b) a median plasma 4-aminopyridine $T_{max}$ in the range of about 3 h to about 14 h; (c) a mean plasma 4-aminopyridine $AUC_{0-36}$ in the range of about 232 ng·h/mL to about 434 ng·h/mL; and (d) a mean plasma 4-aminopyridine $AUC_{0-\infty}$ in the range of about 230 ng·h/mL to about 472 ng·h/mL. In a specific embodiment of the foregoing, the amount of 4-aminopyridine in the sustained release tablet is about 22 mg. $AUC_{0-36}$ is the area under the curve for 0-36 h. In a preferred embodiment, the sustained release tablet which is characterized by the foregoing pharmacokinetic parameters is a tablet in which 4-aminopyridine is present only in the compressed core (which tablet can be the final oral dosage form of a tablet that does not have an immediate release drug overcoat, or can be the tablet that has not yet been coated with the drug overcoat in an embodiment where the final oral dosage form will have a drug overcoat).

In another specific embodiment, a sustained release 4-aminopyridine tablet as disclosed herein, upon oral administration to human subjects in a fed state, provides one or more of the following pharmacokinetic parameters: (a) a mean plasma 4-aminopyridine $C_{max}$ in the range of about 13.73 ng/mL to about 24.07 ng/mL; (b) a median plasma 4-aminopyridine $T_{max}$ in the range of about 6 h to about 21 h; (c) a mean plasma 4-aminopyridine $AUC_{0-36}$ in the range of about 216 ng·h/mL to about 472 ng·h/mL; and (d) a mean plasma 4-aminopyridine $AUC_{0-\infty}$ in the range of about 218 ng·h/mL to about 490 ng·h/mL. In a specific embodiment of the foregoing, the amount of 4-aminopyridine in the sustained release tablet is about 22 mg. In a preferred embodiment, the sustained release tablet which is characterized by the foregoing pharmacokinetic parameters is a tablet in which 4-aminopyridine is present only in the compressed core (which tablet can be the final oral dosage form of a tablet that does not have an immediate release drug overcoat, or can be the tablet that has not yet been coated with the drug overcoat in an embodiment where the final oral dosage form will have a drug overcoat).

5.3 Combination Therapy

In certain embodiments, the sustained release 4-aminopyridine tablet as disclosed herein may be orally administered in combination with one or more additional medicaments. Such combination therapy may be achieved by way of the simultaneous, sequential, or separate dosing of the individual components of the treatment. In one embodiment, the combination therapy is achieved by way of separate dosing of the sustained release 4-aminopyridine tablet and the other medicament.

In certain embodiments, the other medicament is a therapeutic agent effective for the treatment of multiple sclerosis. In specific embodiments, the other medicament is selected from a group consisting of, but not limited to, AVONEX (interferon beta-1a), REBIF (interferon beta-1a), BETASERON and EXTAVIA (interferon beta-1b), COPAXONE (glatiramer acetate), NOVANTRONE (mitoxantrone), TYSABRI (natalizumab), AUBAGIO (teriflunomide), GILENYA (fingolimod), LEMTRADA (alemtuzumab), PLEGRIDY (peginterferon beta-1a), TECFIDERA (dimethyl fumarate), ocrelizumab, prednisone, prednisolone, methylprednisolone, betamethasone, and dexamethasone.

In certain embodiments, the other medicament is a therapeutic agent intended for the prophylaxis of stroke. In specific embodiments, the other medicament is selected from the group consisting of, but not limited to, anticoagulant agents (e.g. aspirin, clopidogrel, etc.) and antihypertensive agents.

6 EXAMPLES

Certain embodiments provided herein are illustrated by the following non-limiting examples.

6.1 Example 1: Preparation of Sustained Release 4-Aminopyridine Tablets 6.1.1 Dispensing, Sifting and Blending 4-Aminopyridine (110.0 g), Kollidon SR Polymer (550.0 g), Polyethylene Oxide, NF (Sentry Polyox WSR 303) (330.0 g), and Dibasic Calcium Phosphate Dihydrate, USP/NF (1188 g) were sifted through a 30 mesh hand screen into a container double-lined with polyethylene bags. The sifted powders obtained above were placed in an 8 quart V-Blender, and blended for 10 minutes. To this blended mixture was added Magnesium Stearate, NF Non-Bovine Hyqual (22.0 g) that was sifted through a 20 mesh hand screen. The entire mixture was blended for additional 5 minutes, and then the blend was discharged into a container lined with two polyethylene bags after performing content uniformity and physical testing on the final blend.

6.1.2 Tableting

The completed blend from above was fed into a tablet press hopper. A rotary tablet press (power assisted) was set up with a tablet deduster and metal detector in-line. Batch set-up parameters were then determined to achieve tablets a target weight of 440 mg (individual range 407-473 mg).

The blend was then compressed using a Compact-19 Tablet Press with Tooling Set No. 138 to furnish the desired core tablets, while performing checks on individual tablet weight, mean tablet weight, hardness, thickness, appearance and friability at defined times during the compression run. The weight of the desired tablets was within +/−7.5% of theoretical tablet weight of 440 mg (i.e., within 407.0-473.0 mg).

6.1.3 Coating and Curing

Purified Water (686.0 g) was weighed into a suitable solution tank. The Purified Water was mixed with Ethylcellulose Dispersion Type B, NF (Surelease E-7-19040, Clear) (1030 g) while stirring using an overhead mixer with a suitable impeller. Mixing was continued for at least 15 minutes with low to moderate agitation, while ensuring there are no visual signs for any lumps, foam, settling, etc. prior to coating.

The core tablets prepared in Section 6.1.2 were loaded into a LabCoat MX tablet coater equipped with a 15" pan, a peristaltic pump with new tubing (Maserflex Pt/Si Size 14) and a single spray gun. The tablets were pre-warm for approximately 10 minutes by jogging the pan with the fan and heater on at 50° C. After setting the Supply Temperature to target 60° C., the above prepared film-coat was applied in a controlled manner to the pre-warmed core tablets in the Labcoat MX to approximately 9% weight gain (i.e., 39.6 mg). The coated tablets thus formed were then subjected to a curing step by drying them at 55° C. for 1 hour and then allowed to cool for at least 5 minutes to a target exhaust temperature of approximately 25-30° C. while jogging the pan. The tablets were then discharged into a suitable container lined with two polyethylene bags to afford the final coated tablets.

Table 1 provides the amounts and weight percentages of ingredients present in the sustained release tablet prepared using the method described above.

TABLE 1

Composition of sustained release tablets containing 22 mg 4-aminopyridine and 9% ethylcellulose coat by weight of the compressed core

| Ingredient | % w/w of compressed core | Amount per tablet (mg) |
|---|---|---|
| Compressed Core | | |
| 4-aminopyridine | 5.0 | 22.0 |
| KOLLIDON ® SR | 25.0 | 110.0 |
| Polyethylene oxide (Sentry Polyox WSR 303) | 15.0 | 66.0 |
| Dibasic calcium phosphate dihydrate | 54.0 | 237.6 |
| Magnesium stearate | 1.0 | 4.4 |
| Weight of Compressed Core | 100 | 440 |
| Functional Coating | | |
| Ethylcellulose Dispersion Type B | 9 | 39.6 |

Thus, for the sustained release tablet of Example 1, containing 22 mg 4-aminopyridine (i.e., 5% w/w of the compressed cored) and 9% ethylcellulose coat by weight of the compressed core, the ratio of the amount of the ethylcellulose coat to the amount of 4-aminopyridine is 1.8:1; wherein for calculating said ratio, the amount of the ethylcellulose coat is the weight percentage of the ethylcellulose coat by weight of the compressed core (i.e., 9%), and the amount of 4-aminopyridine is the weight percentage of 4-aminopyridine by weight of the compressed core (i.e. 5%).

Similarly, for the sustained release tablet of Example 1, containing 22 mg 4-aminopyridine (i.e., 5% w/w of the compressed cored) and 9% ethylcellulose coat by weight of the compressed core, the ratio of the amount of the ethylcellulose coat to the amount of 4-aminopyridine in the compressed core is about 0.4:1; wherein for calculating said ratio, the amount of the ethylcellulose coat is the weight percentage of the ethylcellulose coat by weight of the compressed core (i.e., 9%), and the amount of 4-aminopyridine is the weight in milligrams of 4-aminopyridine (i.e., 22 mg).

The dissolution profile of the sustained release tablet in Example 1 is shown in FIG. 1. The dissolution profile was generated using the conditions shown in Table 2 below.

TABLE 2

Dissolution profile parameters

| Apparatus | USP Type II (Paddles) |
|---|---|
| Paddle Speed | 50 RPM |
| Dissolution Medium | 50 mM Phosphate Buffer, pH 6.8 |
| Dissolution Medium Temperature | 37.0 ± 0.5° C. |
| Sampling Time Profile | 1, 2, 4, 6, 8, 10, 12, 14, 18, and 24 hours |
| Vessel Volume | 900 mL |
| UV Wavelength | 262 nm |
| Cell | 1 mm, quartz |
| Sinkers | QLA, 2S |

At each sampling time point, a 10 mL sample aliquot was removed from each vessel and collected in a test tube. Each sample aliquot was filtered through a 0.45 µm nylon syringe filter. The first 2 mL of the filtrate was discarded, and the remaining filtrate was collected for UV analysis.

Figure 2:
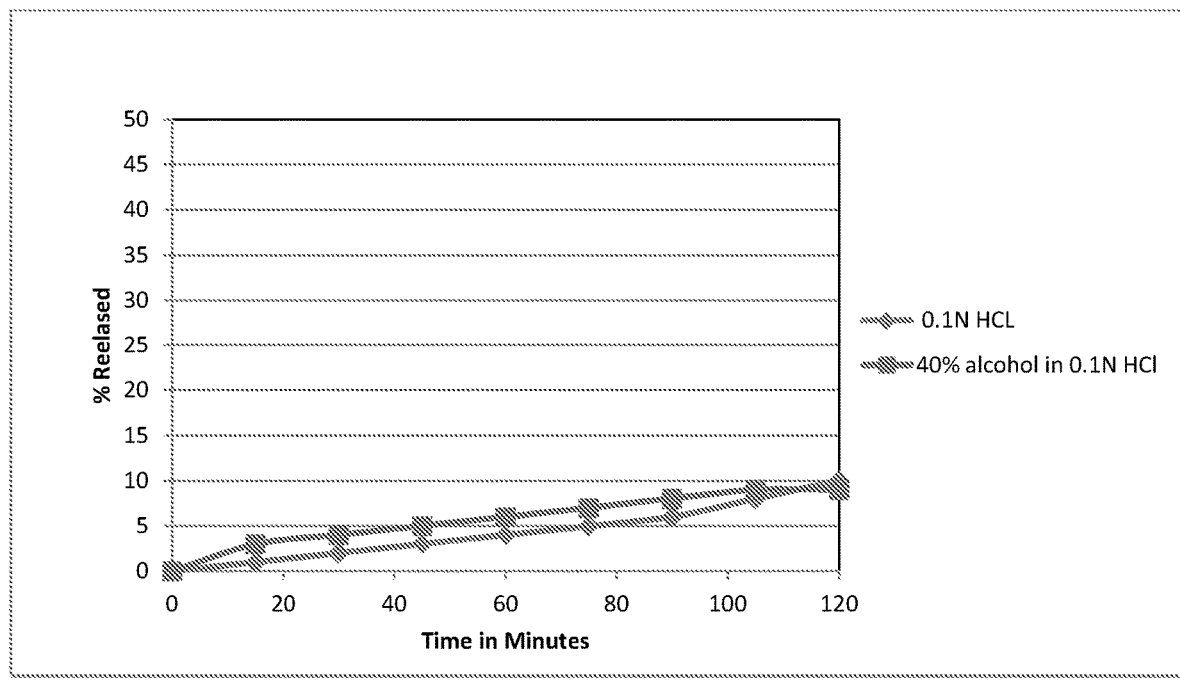
FIG. 2 depicts dissolution profiles of the sustained release tablet in Example 1 employing 0.1 N hydrochloric acid as a dissolution medium with and without 40% alcohol (ethanol).

To test alcohol dose dumping, dissolution for 2 hours was performed by employing 0.1 N HCl containing 40% alcohol (ethanol) as a dissolution medium. The results are shown in FIG. 2.

6.2 Example 2: Sustained Release Tablets Containing 22 mg 4-Aminopyridine and Coated to 8%, 9%, and 10% weight gain Core tablets (i.e., compressed cores) containing 22 mg 4-aminopyridine were prepared using the formulation described in Table 1 and the method described in Example 1, Sections 6.1.1 and 6.1.2. These core tablets were coated with an aqueous Ethylcellulose Dispersion Type B (Surelease E-7-19040, Clear) coat to approximately 8% and 10% weight gain, following the procedure described in Example 1, Section 6.1.3. A comparison of the dissolution profiles (generated using the parameters shown in Table 2) of the sustained release tablets containing 22 mg 4-aminopyridine, coated with an aqueous Ethylcellulose Dispersion Type B coat to approximately 8% (Example 2), 9% (tablets generated pursuant to Example 1), and 10% (Example 2) weight gain, is shown in FIG. 3 and Table 3.

TABLE 3

Dissolution profiles of sustained release tablets containing 22 mg 4-aminopyridine, coated to 8%, 9%, and 10% weight gain

| Coat | % 4AP released | | | | | | | | | | |
|---|---|---|---|---|---|---|---|---|---|---|---|
| % | 0 h | 1 h | 2 h | 4 h | 6 h | 8 h | 10 h | 12 h | 14 h | 18 h | 24 h |
| 8% | 0 | 2 | 9 | 21 | 37 | 52 | 64 | 74 | 82 | 90 | 99 |
| 9% | 0 | 2 | 8 | 21 | 36 | 50 | 62 | 72 | 80 | 90 | 97 |
| 10% | 0 | 2 | 8 | 20 | 35 | 48 | 60 | 71 | 78 | 88 | 97 |

6.3 Example 3: Preparation of Sustained Release Tablets Containing 16.5 mg 4-Aminopyridine Sustained release tablets containing 16.5 mg 4-aminopyridine were prepared using the method described in Example 1, except using the amounts and weight percentages of ingredients shown in Table 4.

TABLE 4

Composition of sustained release tablets containing 16.5 mg 4-aminopyridine and 6% ethylcellulose coat by weight of the compressed core

| Ingredient | % w/w of compressed core | Amount per tablet (mg) |
|---|---|---|
| Compressed Core | | |
| 4-aminopyridine | 3.75 | 16.5 |
| KOLLIDON ® SR | 25.0 | 110.0 |
| Polyethylene oxide (Sentry Polyox WSR 303) | 15.0 | 66.0 |
| Dibasic calcium phosphate dihydrate | 55.25 | 243.1 |
| Magnesium stearate | 1.0 | 4.4 |
| Weight of Compressed Core | 100 | 440 |
| Functional Coating | | |
| Ethylcellulose Dispersion Type B | 6 | 26.4 |

Thus, for the sustained release tablet containing 16.5 mg 4-aminopyridine (i.e., 3.75% w/w of the compressed cored) and 6% ethylcellulose coat by weight of the compressed core, the ratio of the amount of the ethylcellulose coat to the amount of 4-aminopyridine is 1.6:1; wherein for calculating said ratio, the amount of the ethylcellulose coat is the weight percentage of the ethylcellulose coat by weight of the compressed core (i.e., 6%), and the amount of 4-aminopyridine is the weight percentage of 4-aminopyridine by weight of the compressed core (i.e. 3.75%).

Similarly, for the sustained release tablet containing 16.5 mg 4-aminopyridine (i.e., 3.75% w/w of the compressed cored) and 6% ethylcellulose coat by weight of the compressed core, the ratio of the amount of the ethylcellulose coat to the amount of 4-aminopyridine in the compressed core is about 0.35:1; wherein for calculating said ratio, the amount of the ethylcellulose coat is the weight percentage of the ethylcellulose coat by weight of the compressed core (i.e., 6%), and the amount of 4-aminopyridine is the weight in milligrams of 4-aminopyridine (i.e., 16.5 mg).

In addition, the core tablets prepared using the formulation described in Table 4 were coated with an aqueous Ethylcellulose Dispersion Type B (Surelease E-7-19040, Clear) coat to approximately 5% and 7% weight gain. A comparison of the dissolution profiles (generated using the parameters shown in Table 2) of the sustained release tablets containing 16.5 mg 4-aminopyridine, coated with an aqueous Ethylcellulose Dispersion Type B coat to approximately 5%, 6%, and 7% weight gain, is shown in FIG. 4 and Table 5.

TABLE 5

Dissolution profiles of sustained release tablets containing 16.5 mg 4-aminopyridine, coated to 5%, 6%, and 7% weight gain

| Coat | % 4AP released | | | | | | | | | | |
|---|---|---|---|---|---|---|---|---|---|---|---|
| % | 0 h | 1 h | 2 h | 4 h | 6 h | 8 h | 10 h | 12 h | 14 h | 18 h | 24 h |
| 5% | 0 | 6 | 16 | 35 | 51 | 63 | 73 | 81 | 87 | 94 | 98 |
| 6% | 0 | 5 | 14 | 30 | 46 | 59 | 69 | 77 | 84 | 91 | 96 |
| 7% | 0 | 3 | 10 | 24 | 40 | 53 | 64 | 74 | 81 | 89 | 98 |

6.4 Example 4: Preparation of Sustained Release Tablets Containing 22 mg 4-Aminopyridine and Coated to 5% Weight Gain 6.4.1 Dispensing, Sifting and Blending 4-Aminopyridine (5000.0 g), Kollidon SR Polymer (25000.0 g), Polyethylene Oxide, NF (Sentry Polyox WSR 303) (15000.0 g), and Dibasic Calcium Phosphate Dihydrate, USP/NF (54000.0 g) were sifted through a 30 mesh hand screen into a container double-lined with polyethylene bags. The sifted powders obtained above were placed in an 8.5 cu foot tote, and blended for 5 minutes. To this blended mixture was added Magnesium Stearate, NF Non-Bovine Hyqual (1000.0 g) that was sifted through a 20 mesh hand screen. The entire mixture was blended for additional 19 minutes, and then the blend was discharged into a container lined with two polyethylene bags after performing blend uniformity and physical testing on the final blend.

6.4.2 Tableting

The completed blend from above was fed into a tablet press hopper. A single rotary tablet press (power assisted) was set up with a tablet deduster and metal detector in-line. Batch set-up parameters were then determined to achieve tablets a target weight of 440 mg (individual range 407-473 mg).

The blend was then compressed using a Fette 1200i Tablet Press with Tooling Set No. 138 to furnish the desired core tablets, while performing checks on individual tablet weight, mean tablet weight, hardness, thickness, appearance and friability at defined times during the compression run. The weight of the desired tablets was within +/−7.5% of theoretical tablet weight of 440 mg (i.e., within 407.0-473.0 mg).

6.4.3 Coating and Curing

Purified Water (31200.0 g) was weighed into a suitable solution tank. The Purified Water was mixed with Ethylcellulose Dispersion Type B, NF (Surelease E-7-19040, Clear) (46800 g) while stirring using an overhead mixer with a suitable impeller. Mixing was continued for at least 15 minutes with low to moderate agitation, while ensuring there are no visual signs for any lumps, foam, settling, etc. prior to coating.

The core tablets prepared in the above section were loaded into a O'Hara fastcoat48 tablet coater equipped with a 48" pan, a peristaltic pump with a new tubing (Maserflex Pt/Si Size 35) and 4 spray guns. The tablets were pre-warmed for approximately 10 minutes by jogging the pan with the fan and heater on at 50° C. After setting the Supply Temperature to target 65° C., the above prepared film-coat was applied in a controlled manner to the pre-warmed core tablets in the O'Hara fastcoat48 tablet coater to approximately 5% weight gain (i.e., 22.0 mg). The coated tablets thus formed were then subjected to a curing step by drying them at 55° C. for 1 hour and then allowed to cool for at least 5 minutes to a target exhaust temperature of approximately 25-30° C. while jogging the pan. The tablets were then discharged into a suitable container lined with two polyethylene bags to afford the final coated tablets.

Table 6 provides the amounts and weight percentages of ingredients present in the sustained release tablet prepared using the method described above:

TABLE 6

Composition of sustained release tablets containing 22 mg 4-aminopyridine and 5% ethylcellulose coat by weight of the compressed core

| Ingredient | % w/w of compressed core | Amount per tablet (mg) |
|---|---|---|
| Compressed Core | | |
| 4-aminopyridine | 5.0 | 22.0 |
| KOLLIDON ® SR | 25.0 | 110.0 |
| Polyethylene oxide (Sentry Polyox WSR 303) | 15.0 | 66.0 |
| Dibasic calcium phosphate dihydrate | 54.0 | 237.6 |
| Magnesium stearate | 1.0 | 4.4 |
| Weight of Compressed Core | 100 | 440 |
| Functional Coating | | |
| Ethylcellulose Dispersion Type B | 5 | 22.0 |

The dissolution profile (generated using the conditions shown in Table 2) of the sustained release tablet in Example 4 is shown in FIG. 5.

6.5 Example 5: Pharmacokinetic Studies

A study was conducted evaluating the effect of food on the pharmacokinetics of the prototype 22 mg 4-aminopyridine sustained release tablet prepared as described in Example 1, following oral administration of a single dose in healthy human subjects. In the study, subjects observed an overnight fast of at least 10 hours prior to dosing. The following morning, a single dose was orally administered with 240 mL water. The dose was administered on an empty stomach in the fasted condition (N=20) and following a standard high fat-high content meal (see, Guidance for Industry: Food-Effect Bioavailability and Fed Bioequivalence Studies, Food and Drug Administration, Center for Drug Evaluation and Research (CDER), December 2002) in the fed condition (N=20).

A summary of the pharmacokinetic parameters for dalfampridine following oral administration of the 22 mg prototype tablet of Example 1 in healthy human subjects in fed (N=20) and fasted (N=20) states is presented in Table 7. Mean $C_{max}$ and AUC values were comparable following administration in both fed and fasted states.

Following administration of the prototype formulation in the fed state, absorption was slightly delayed than that of the fasted state, median $t_{max}$ of 12.0 and 7.50 hours, respectively. There were no other notable differences in the pharmacokinetics of the prototype formulation when administered in the fed versus the fasted state.

TABLE 7

Summary of Pharmacokinetic Parameters of Dalfampridine Following Administration of a Single Oral Dose of the 22 mg 4-Aminopyridine Sustained Release Tablet of Example 1 in Healthy Human Subjects in Fed or Fasted States

| Pharmacokinetic Parameter (units) | Prototype-Fed Arithmetic Mean ± SD (N = 20) | Prototype-Fasted Arithmetic Mean ± SD (N = 20) |
|---|---|---|
| $C_{max}$ (ng/mL) | 18.9 ± 5.17 | 17.7 ± 2.96 |
| $AUC_{0-last}$ (ng · hr/mL) | 342 ± 131 | 330 ± 104 |
| $AUC_{0-36}$ (ng · hr/mL) | 344 ± 128 | 333 ± 101 |
| $AUC_{0-\infty}$ (ng · hr/mL) | 354 ± 136 | 351 ± 121 |
| $t_{max}$ (hr)[a] | 12.0 [6.0, 21.0] | 7.50 [3.0, 14.0] |
| $t_{lag}$ (hr)[a] | 1.0 [0, 2.0] | 0.50 [0, 1.0] |
| $\lambda_z$ (1/hr)[b] | 0.176 ± 0.0331 | 0.172 ± 0.0551 |
| $t_{1/2}$ (hr) | 4.1 ± 0.87 | 4.7 ± 2.30 |

[a]Median [min, max] reported for $t_{max}$ and $t_{lag}$; $t_{lag}$ is defined as time prior to the first measurable (non-zero) plasma concentration
[b]$\lambda_z$ is defined as aparent elimination rate constant The mean plasma concentrations over time are shown in FIG. 6, which demonstrates that sustained plasma levels are achieved over a 24-hour period with a single dose. These sustained plasma levels demonstrate feasibility of once-daily dosing.

INCORPORATION BY REFERENCE

Various references such as patents, patent applications, and publications are cited herein, the disclosures of which are hereby incorporated by reference herein in their entireties.

The invention claimed is:

1. A sustained release tablet comprising:
(a) a compressed core, said compressed core comprising (i) 4-aminopyridine, wherein the amount of 4-aminopyridine in the compressed core is in the range of about 1% w/w to about 10% w/w of the compressed core, (ii) a polyethylene oxide with a molecular weight between 4,000,000 and 8,000,000, wherein the amount of the polyethylene oxide in the compressed core is in the range of about 10% w/w to about 20% w/w of the compressed core, and (iii) a mixture comprising polyvinyl acetate and polyvinyl pyrrolidone, wherein the amount of the mixture comprising polyvinyl acetate and polyvinyl pyrrolidone in the compressed core is in the range of about 20% w/w to about 30% w/w of the compressed core; and
(b) an amount of an ethylcellulose coat surrounding said compressed core, said amount of the ethylcellulose coat being in the range of about 5% w/w to about 10% w/w of the compressed core.

2. The sustained release tablet of claim 1, wherein said mixture further comprises one or more pharmaceutically acceptable excipients.

3. The sustained release tablet of claim 1, wherein said mixture consists of about 80% polyvinyl acetate, about 19% polyvinyl pyrrolidone, about 0.8% sodium lauryl sulfate, and about 0.2% silica.

4. The sustained release tablet of claim 1, wherein the compressed core further comprises a filler and a lubricant.

5. The sustained release tablet of claim 1, wherein the polyethylene oxide has a molecular weight of 7,000,000.

6. The sustained release tablet of claim 1, wherein said mixture consists of about 80% polyvinyl acetate, about 19% polyvinyl pyrrolidone, about 0.8% sodium lauryl sulfate, and about 0.2% of silica; wherein the compressed core further comprises dibasic calcium phosphate dihydrate and magnesium stearate; and wherein the amount of 4-aminopyridine is in the range of about 4% w/w to about 6% w/w of the compressed core.

7. The sustained release tablet of claim 1, wherein the amount of the ethylcellulose coat surrounding the compressed core is about 9% w/w of the compressed core.

8. The sustained release tablet of claim 1, wherein the amount of the ethylcellulose coat is in the range of about 5% w/w to about 7% w/w of the compressed core.

9. The sustained release tablet of claim 8, wherein the amount of 4-aminopyridine is in the range of about 3% w/w to about 5% w/w of the compressed core and the amount of the ethylcellulose coat surrounding the compressed core is about 6% w/w of the compressed core.

10. The sustained release tablet of claim 1, wherein the amount of 4-aminopyridine in the compressed core is in the range of about 12 mg to about 25 mg.

11. The sustained release tablet of claim 1, wherein the amount of 4-aminopyridine in the compressed core is in the range of about 5 mg to about 12 mg.

12. The sustained release tablet of claim 1, wherein (i) the amount of 4-aminopyridine is in the range of about 4% w/w to about 6% w/w of the compressed core; (ii) the mixture consists of about 80% polyvinyl acetate, about 19% polyvinyl pyrrolidone, about 0.8% sodium lauryl sulfate, and about 0.2% of silica; (iii) the amount of the mixture is in the range of about 20% w/w to about 30% w/w of the compressed core; and (iv) the compressed core further comprises (A) dibasic calcium phosphate dihydrate, wherein the amount of dibasic calcium phosphate dihydrate is in the range of about 50% w/w to about 60% w/w of the compressed core; and (B) magnesium stearate, wherein the amount of magnesium stearate is in the range of about 0.7% w/w to about 1.3% w/w of the compressed core.

13. The sustained release tablet of claim 1, wherein (i) the amount of 4-aminopyridine is in the range of about 4% w/w to about 6% w/w of the compressed core; (ii) the polyethylene oxide has a molecular weight of 7,000,000, wherein the amount of the polyethylene oxide is about 15% w/w of the compressed core; (iii) the mixture consists of about 80% polyvinyl acetate, about 19% polyvinyl pyrrolidone, about 0.8% sodium lauryl sulfate, and about 0.2% of silica, wherein the amount of the mixture is about 25% w/w of the compressed core; (iv) the compressed core further comprises (A) dibasic calcium phosphate dihydrate, wherein the amount of dibasic calcium phosphate dihydrate is about 54% w/w of the compressed core; and (B) magnesium stearate, wherein the amount of magnesium stearate is about 1% w/w of the compressed core; and wherein the amount of the ethylcellulose coat is about 9% w/w of the compressed core.

14. The sustained release tablet of claim 13, wherein the amount of 4-aminopyridine is about 22 mg.

15. The sustained release tablet of claim 1, wherein (i) the amount of 4-aminopyridine is in the range of about 3% w/w to about 5% w/w of the compressed core; (ii) the mixture consists of about 80% polyvinyl acetate, about 19% polyvinyl pyrrolidone, about 0.8% sodium lauryl sulfate, and about 0.2% of silica; (iii) the amount of the mixture is in the range of about 20% w/w to about 30% w/w of the compressed core; (iv) the compressed core further comprises (A) dibasic calcium phosphate dihydrate, wherein the amount of dibasic calcium phosphate dihydrate is in the range of about 50% w/w to about 60% w/w of the compressed core; and (B) magnesium stearate, wherein the amount of magnesium stearate is in the range of about 0.7% w/w to about 1.3% w/w of the compressed core; and wherein the amount of the ethylcellulose coat is in the range of about 5% w/w to about 7% w/w of the compressed core.

16. The sustained release tablet of claim 1, wherein (i) the amount of 4-aminopyridine is in the range of about 3% w/w to about 5% w/w of the compressed core; (ii) the polyethylene oxide has a molecular weight of 7,000,000, wherein the amount of the polyethylene oxide is about 15% w/w of the compressed core; (iii) the mixture consists of about 80% polyvinyl acetate, about 19% polyvinyl pyrrolidone, about 0.8% sodium lauryl sulfate, and about 0.2% of silica, wherein the amount of the mixture is about 25% w/w of the compressed core; (iv) the compressed core further comprises (A) dibasic calcium phosphate dihydrate, wherein the amount of dibasic calcium phosphate dihydrate is about 55% w/w of the compressed core; and (B) magnesium stearate, wherein the amount of magnesium stearate is about 1% w/w of the compressed core; and wherein the amount of the ethylcellulose coat is about 6% w/w of the compressed core.

17. The sustained release tablet of claim 16, wherein the amount of 4-aminopyridine is about 16.5 mg.

18. The sustained release tablet of claim 1, wherein the sustained release tablet is the product of a process comprising a curing step after coating the compressed core with ethylcellulose, and wherein said curing step comprises heating the coated compressed core to a temperature above 23° C. for a period of time of at least 15 minutes.

19. The sustained release tablet of claim 1, wherein the sustained release tablet does not further comprise an immediate release drug overcoat containing 4-aminopyridine.

20. The sustained release tablet of claim 1, wherein the sustained release tablet provides a zero-order or near-zero-order release of the 4-aminopyridine.

21. The sustained release tablet of claim 1, wherein the sustained release tablet is suitable for once daily oral administration.

22. The sustained release tablet of claim 1, wherein the sustained release tablet comprises an amount of 4-aminopyridine that is therapeutically effective over a period of 24 hours upon oral administration to a human patient.

23. The sustained release tablet of claim 1, wherein the release of the 4-aminopyridine, upon subjecting the tablet to an in vitro dissolution test employing 50 mM Phosphate Buffer, pH 6.8 as dissolution medium, is as follows:
within the first 2 hours after the start of the test at most 30% w/w of the total amount of the 4-aminopyridine contained in the sustained release tablet is released.

24. The sustained release tablet of claim 23, wherein the release of the 4-aminopyridine is as follows:
within the first 24 hours after the start of the test at least 80% w/w of the total amount of the 4-aminopyridine contained in the sustained release tablet is released.

25. The sustained release tablet of claim 1, wherein the sustained release tablet further comprises an immediate release drug overcoat containing 4-aminopyridine.

26. The sustained release tablet of claim 1, wherein the amount of the ethylcellulose coat is in the range of about 8% w/w to about 10% w/w of the tablet, wherein said tablet is the product of a process comprising a curing step after coating the compressed core with ethylcellulose, and wherein said curing step comprises heating the coated compressed core to a temperature above 23° C. for a period of time of at least 15 minutes.

27. The sustained release tablet of claim 18, wherein said curing step comprises exposing the coated compressed core to a temperature in the range of 40-70° C. for a period of time of at least 1 hour.

28. The sustained release tablet of claim 1, wherein the release of the 4-aminopyridine, upon subjecting the tablet to an in vitro dissolution test employing 50 mM Phosphate Buffer, pH 6.8 as dissolution medium, is as follows:
   within the first 2 hours after the start of the test at most 20% w/w of the total amount of the 4-aminopyridine contained in the sustained release tablet is released.

29. The sustained release tablet of claim 28, wherein the release of the 4-aminopyridine is as follows:
   within the first 24 hours after the start of the test at least 80% w/w of the total amount of the 4-aminopyridine contained in the sustained release tablet is released.

30. A sustained release tablet comprising:
   (a) a compressed core, said compressed core comprising (i) 4-aminopyridine, wherein the amount of 4-aminopyridine in the compressed core is in the range of about 1% w/w to about 10% w/w of the compressed core, (ii) a polyethylene oxide with a molecular weight between 4,000,000 and 8,000,000, wherein the amount of the polyethylene oxide in the compressed core is in the range of about 10% w/w to about 20% w/w of the compressed core, and (iii) a mixture comprising polyvinyl acetate and polyvinyl pyrrolidone, wherein the amount of the mixture comprising polyvinyl acetate and polyvinyl pyrrolidone in the compressed core is in the range of about 20% w/w to about 30% w/w of the compressed core; and
   (b) an amount of an ethylcellulose coat surrounding said compressed core, wherein the ratio of the amount of the ethylcellulose coat to the amount of 4-aminopyridine in the compressed core is in the range of about 0.5:1 to about 3:1; wherein for calculating said ratio, the amount of the ethylcellulose coat is the weight percentage of the ethylcellulose coat by weight of the compressed core, and the amount of 4-aminopyridine is the weight percentage of 4-aminopyridine by weight of the compressed core.

31. A sustained release tablet comprising:
   (a) a compressed core, said compressed core comprising (i) 4-aminopyridine, wherein the amount of 4-aminopyridine in the compressed core is in the range of about 1% w/w to about 10% w/w of the compressed core, (ii) a polyethylene oxide with a molecular weight between 4,000,000 and 8,000,000, wherein the amount of the polyethylene oxide in the compressed core is in the range of about 10% w/w to about 20% w/w of the compressed core, and (iii) a mixture comprising polyvinyl acetate and polyvinyl pyrrolidone, wherein the amount of the mixture comprising polyvinyl acetate and polyvinyl pyrrolidone in the compressed core is in the range of about 20% w/w to about 30% w/w of the compressed core; and
   (b) an amount of an ethylcellulose coat surrounding said compressed core, wherein the ratio of the amount of the ethylcellulose coat to the amount of 4-aminopyridine in the compressed core is in the range of about 0.1:1 to about 0.7:1;
   wherein for calculating said ratio, the amount of the ethylcellulose coat is the weight percentage of the ethylcellulose coat by weight of the compressed core, and the amount of 4-aminopyridine is the weight in milligrams of 4-aminopyridine.

32. A method of making a sustained release tablet comprising 4-aminopyridine, which method comprises:
   (a) forming a compressed core comprising (i) 4-aminopyridine, (ii) a polyethylene oxide with a molecular weight between about 1,000,000 and 10,000,000, (iii) a mixture comprising polyvinyl acetate and polyvinyl pyrrolidone; (iv) dibasic calcium phosphate dihydrate, and (v) magnesium stearate;
   (b) coating the compressed core with an amount of ethylcellulose to form a coated compressed core, said amount of the ethylcellulose coat being in the range of about 5% w/w to about 10% w/w of the compressed core; and
   (c) curing the coated compressed core by exposing it to a temperature in the range of 40-70° C. for a period of time of at least 1 hour.

* * * * *